US008657737B2

(12) United States Patent
Saito

(10) Patent No.: US 8,657,737 B2
(45) Date of Patent: Feb. 25, 2014

(54) ELECTRONIC ENDOSCOPE SYSTEM, AN ELECTRONIC ENDOSCOPE PROCESSOR, AND A METHOD OF ACQUIRING BLOOD VESSEL INFORMATION

(75) Inventor: Takaaki Saito, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 293 days.

(21) Appl. No.: 13/016,531

(22) Filed: Jan. 28, 2011

(65) Prior Publication Data

US 2011/0230715 A1 Sep. 22, 2011

(30) Foreign Application Priority Data

Mar. 19, 2010 (JP) ................................. 2010-064049

(51) Int. Cl.
*A61B 1/06* (2006.01)

(52) U.S. Cl.
USPC ........................... 600/160; 600/178; 600/323

(58) Field of Classification Search
USPC ................................................. 600/339, 323
See application file for complete search history.

(56) References Cited

U.S. PATENT DOCUMENTS

| 5,001,556 | A | * | 3/1991 | Nakamura et al. | 348/70 |
| 5,078,150 | A | * | 1/1992 | Hara et al. | 600/476 |
| 5,956,416 | A | * | 9/1999 | Tsuruoka et al. | 382/128 |
| 5,974,338 | A | * | 10/1999 | Asano et al. | 600/323 |
| 5,983,120 | A | * | 11/1999 | Groner et al. | 600/310 |
| 7,539,335 | B2 | * | 5/2009 | Fukuyama | 382/128 |
| 7,711,403 | B2 | * | 5/2010 | Jay et al. | 600/407 |
| 7,912,534 | B2 | * | 3/2011 | Grinvald et al. | 600/476 |
| 2009/0247881 | A1 | * | 10/2009 | Maeda et al. | 600/476 |

FOREIGN PATENT DOCUMENTS

| JP | 2648494 B2 | 8/1997 |
| JP | 2001-37718 A | 2/2001 |

* cited by examiner

*Primary Examiner* — Anhtuan T Nguyen
*Assistant Examiner* — Jae Woo
(74) *Attorney, Agent, or Firm* — Birch, Stewart, Kolasch & Birch, LLP

(57) ABSTRACT

The system includes an illuminating unit, an electronic endoscope, a unit for outputting first image data having different wavelength bands from the imaging signal, a unit for producing blood vessel information from the first image data, a unit for setting a given region in an image as reference value region, a unit for calculating a reference value for the blood vessel information based on second image data for a region within a reference value region, a unit for calculating relative value blood vessel information from the difference between the blood vessel information and the reference value blood vessel information, a unit for producing a simulated-color relative value blood vessel information image from the relative value blood vessel information, and a monitor for displaying a relative value blood vessel information image.

13 Claims, 13 Drawing Sheets

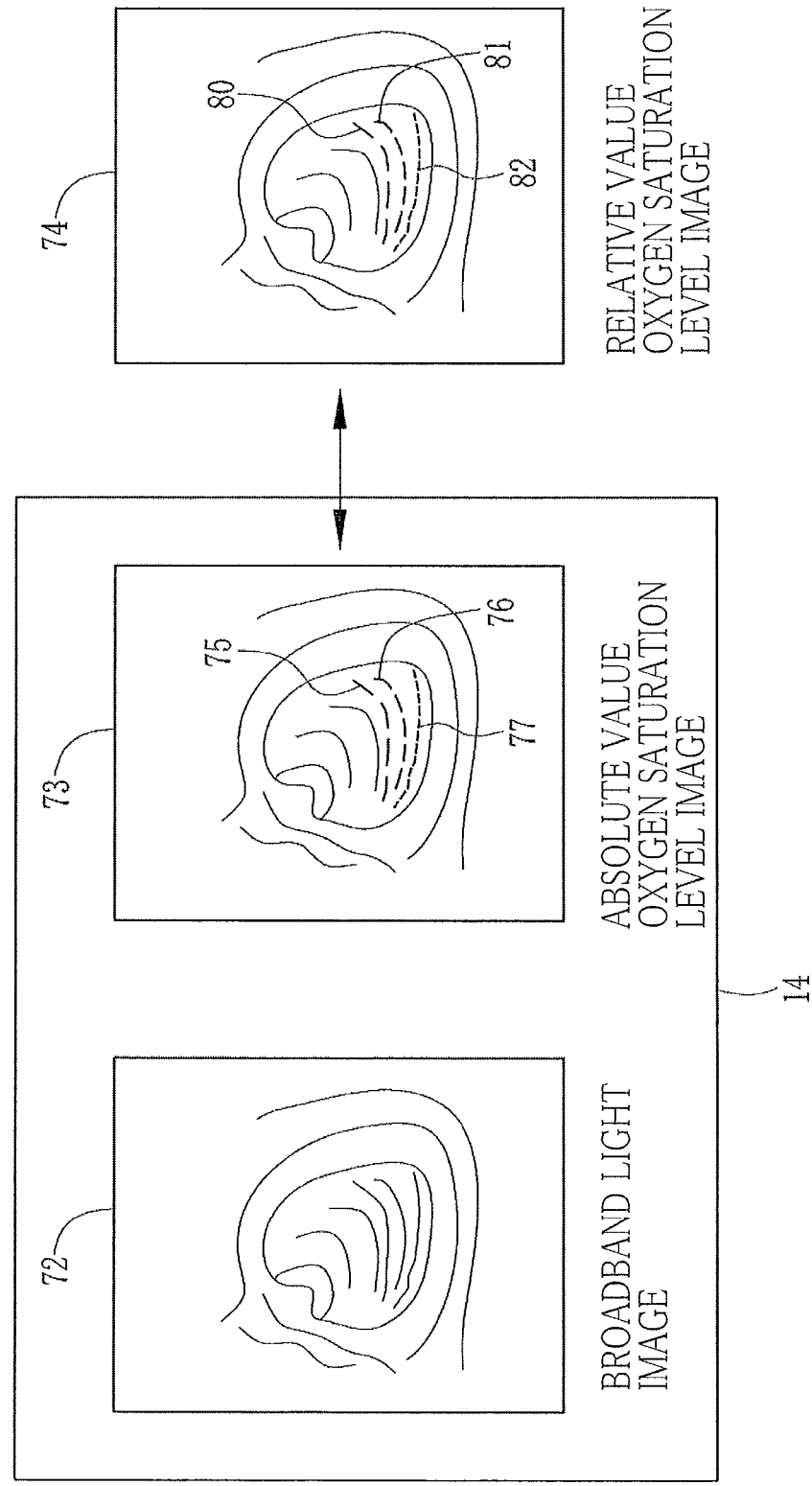

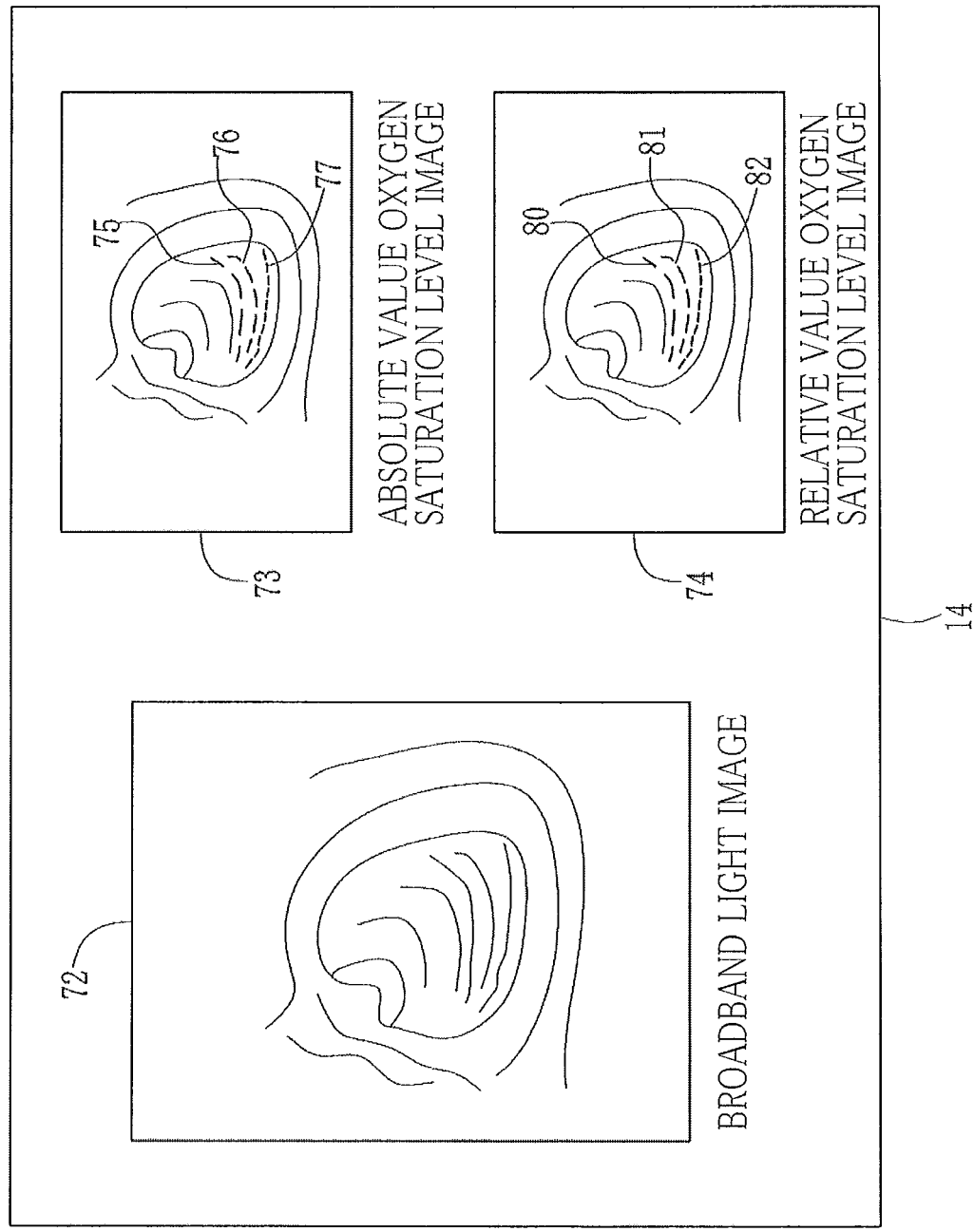

ELECTRONIC ENDOSCOPE SYSTEM, AN ELECTRONIC ENDOSCOPE PROCESSOR, AND A METHOD OF ACQUIRING BLOOD VESSEL INFORMATION

BACKGROUND OF THE INVENTION

The present invention relates to an electronic endoscope system, an electronic endoscope processor, and a method of acquiring blood vessel information for acquiring information on a blood vessel from an image acquired by an electronic endoscope and producing an image from the acquired information.

In recent years, the field of medicine has been seeing a number of diagnoses and treatments using electronic endoscopes. A typical electronic endoscope is equipped with an elongated insertion section that is inserted into a subject's body cavity. The insertion section has therein incorporated an imager such as a CCD at the tip thereof. The electronic endoscope is connected to a light source device, which emits light that, leaving the tip of the insertion section, illuminates the inside of a body cavity. With the inside of the body cavity illuminated by light, the subject tissue inside the body cavity is imaged by an imager provided at the tip of the insertion section. Images acquired by imaging undergo various kinds of processing by a processor connected to the electronic endoscope before being displayed by a monitor. Thus, the electronic endoscope permits real-time observation of the images showing the inside of the subject's body cavity and thus enables sure diagnoses.

The light source device uses a white light source such as a xenon lamp capable of emitting white broadband light whose wavelength ranges from a blue region to a red region. Use of white broadband light to illuminate the inside of a body cavity permits observing the whole subject tissue from acquired images thereof. However, although images acquired by broadband light illumination permit generally observing the whole subject tissue, there are cases where such images fail to enable clear observation of subject tissues such as extremely small blood vessels, deep-layer blood vessels, pit patters, and uneven surface profiles formed of recesses and bumps. As is known, such subject tissues may be made clearly observable when illuminated by narrowband light having a wavelength limited to a specific range. As is also known, image data obtained by illumination with narrowband light yields various kinds of information on a subject tissue such as oxygen saturation level in a blood vessel.

For example, JP 2001-37718 A describes a device wherein a blood information amount calculator calculates a blood information amount in a subject and a region setting unit sets a given region of an endoscopic image whereupon a simulated image data generator uses the information on the specified region and the calculated blood information amount to produce simulated image data that permits recognition of its quantitative change, and an image synthesizer combines the produced simulated image data with the endoscopic image to produce and output synthesized data.

JP 2648494 B describes illuminating with near-infrared narrow-band light IR1 and IR3 whose vascular absorbances change according to oxygen saturation level and a near-infrared narrowband light IR2 whose vascular absorbance does not change in order to acquire an image each time different light is emitted. Then, images acquired by illuminating with narrowband light IR1 and IR3 whose vascular absorbances change and an image acquired by illuminating with narrowband light IR2 whose vascular absorbance does not change are used to calculate variations in luminance between the images, whereupon the calculated variations in luminance are incorporated in the images in monochrome or simulated color. The image thus produced provides information on an oxygen saturation level in a blood vessel.

SUMMARY OF INVENTION

However, the devices described in JP 2001-37718 A and JP 2648494 B are incapable of calculating a relative value with respect to a reference given by a blood information amount corresponding to a specific region (blood vessel information), and this in some cases presented a problem related to robustness of blood information amount such as, for example, oxygen saturation level.

An object of the present invention is to provide a distribution image with an improved robustness of blood vessel information.

In order to attain the above objects, the invention provides an electronic endoscope system comprising an illuminating means for illuminating a subject tissue located in a body cavity and containing a blood vessel with illumination light, an electronic endoscope including an image sensor for receiving reflected light of the illumination light emitted from the illuminating means to the subject tissue to acquire an image of the subject tissue and outputting an imaging signal representing a luminance of the reflected light, a first image data producing means for outputting a plurality of first image data having different wavelength bands from the imaging signal, a blood vessel information producing means for producing blood vessel information on the blood vessel from the first image data, a reference value region setting means for setting a given region in an image acquired by the electronic endoscope as reference value region, a reference value blood vessel information calculating means for calculating a reference value for the blood vessel information based on second image data for a region within a reference value region set by the reference value region setting means to acquire a reference value blood vessel information, a relative value blood vessel information calculating means for calculating relative value blood vessel information from a difference between the blood vessel information and the reference value blood vessel information, an image producing means for producing a relative value blood vessel information image representing a relative value of the blood vessel information in simulated color from the relative value blood vessel information, and an image displaying means for displaying a relative value blood vessel information image produced by the image producing means.

Preferably, the image producing means further produces an absolute value blood vessel information image representing an absolute value of the blood vessel information in simulated color from the blood vessel information produced by the blood vessel information producing means, wherein the electronic endoscope system further comprises an image switching means for switching between the absolute value blood vessel information image and the relative value blood vessel information image, and wherein the image displaying means displays one of the absolute value blood vessel information image and the relative value blood vessel information image selected by the image switching means.

Preferably, the imaging signal is a first and a second narrowband signal corresponding to first and second narrowband light having different wavelength bands.

Preferably, the imaging signal further comprises a third narrowband signal corresponding to a third narrowband light having a wavelength different from those of the first and the second narrowband light, and wherein the blood vessel information is an oxygen saturation level of blood hemoglobin in the blood vessel.

Preferably, the first and the second narrowband light exhibit different absorbances for oxygenated hemoglobin, which is combined with oxygen, and reduced hemoglobin, which is not combined with oxygen, and include wavelengths producing a difference in absorbance by each hemoglobin according to oxygen saturation level.

Preferably, the first narrowband light has a wavelength range of 440 nm plus or minus 10 nm, the second narrowband light has a wavelength range of 470 nm plus or minus 10 nm, and the third narrowband light has a wavelength range of 400 nm plus or minus 10 nm.

Preferably, the reference value region setting means calculates a first luminance ratio between the first image data respectively corresponding to the first and the third narrowband signals and a second luminance ratio between the first image data respectively corresponding to the second and the third narrowband signals, further calculates blood vessel depth information from the first luminance ratio and the second luminance ratio, distinguishes between superficial-layer blood vessel region and a non-superficial-layer blood vessel region from the blood vessel depth information, and thereby sets the non-superficial-layer blood vessel region as the reference value region.

Preferably, the first narrowband light has a wavelength range of 540 nm plus or minus 10 nm, the second narrowband light has a wavelength range of 560 nm plus or minus 10 nm, and the third narrowband light has a wavelength range of 500 nm plus or minus 10 nm, wherein the reference value setting means further calculates a third luminance ratio between the first image data respectively corresponding to the third and the first narrowband signals, identifies a thick blood vessel region based on the third luminance ratio, sets the thick blood vessel region as the reference value region, and calculates a fourth luminance ratio between the first image data respectively corresponding to the first and the second narrowband signals, and wherein the image producing means produce a relative value oxygen saturation level image based on a distribution of the fourth luminance ratio.

Preferably, the image sensor comprises pixels having three colors, red pixels, green pixels, and blue pixels, each provided with color filters having three colors, red, green, and blue, wherein the imaging signal contains an imaging signal of a green pixel and an imaging signal of a red pixel, and wherein the blood vessel information is a blood level.

Preferably, the reference value region setting means sets as the reference value region a given region entered by an operator of the electronic endoscope system in an image acquired by the electronic endoscope.

In order to attain the above objects, the invention provides a processor for an electronic endoscope comprising a signal receiving means for receiving from the electronic endoscope an imaging signal obtained by imaging reflected light of illumination light illuminating a subject tissue located in a body cavity and containing a blood vessel with an image sensor of the electronic endoscope, the imaging signal representing a luminance of the reflected light, a first image data producing means for outputting a plurality of first image data having different wavelength bands from the imaging signal, a blood vessel information producing means for producing blood vessel information on the blood vessel from the first image data, a reference value region setting means for setting a given region in an image acquired by the electronic endoscope as reference value region, a reference value blood vessel information calculating means for calculating a reference value for the blood vessel information based on second image data for a region within a reference value region set by the reference value region setting means to acquire reference value blood vessel information, a relative value blood vessel information calculating means for calculating relative value blood vessel information from a difference between the blood vessel information and the reference value blood vessel information, an image producing means for producing a relative value blood vessel information image representing a relative value of the blood vessel information in simulated color from the relative value blood vessel information, and an image displaying means for displaying a relative value blood vessel information image produced by the image producing means.

In order to attain the above objects, the invention provides a method of acquiring blood vessel information comprising an illuminating step of illuminating a subject tissue located in a body cavity and containing a blood vessel with illumination light, an imaging step of acquiring an image of the subject tissue by receiving reflected light of illumination light from an illuminating means with which the subject tissue has been illuminated to acquire an imaging signal representing a luminance of the reflected light, a first image data producing step of outputting a plurality of first image data having different wavelength bands from the imaging signal, a blood vessel information producing means for producing blood vessel information on the blood vessel from the first image data, a reference value region setting step of setting a given region in an image acquired by the electronic endoscope as reference value region, a reference value blood vessel information calculating step of calculating a reference value for the blood vessel information based on second image data for a region within a reference value region set by the reference value region setting means to acquire reference value blood vessel information, a relative value blood vessel information calculating step of calculating relative value blood vessel information from a difference between the blood vessel information and the reference value blood vessel information, an image producing step of producing a relative value blood vessel information image representing a relative value of the blood vessel information in simulated color from the relative value blood vessel information, and an image displaying step of displaying a relative value blood vessel information image produced by the image producing means.

In order to attain the above objects, the invention provides a pathological observation device comprising an illuminating means for illuminating a subject tissue located in a body cavity and containing a blood vessel with illumination light, an observing means including an image sensor for receiving reflected light of the illumination light emitted from the illuminating means to the subject tissue, acquiring an image of the subject tissue, and outputting an imaging signal representing a luminance of the reflected light, a first image data producing means for outputting a plurality of first image data having different wavelength bands from the imaging signal, a blood vessel information producing means for producing blood vessel information on the blood vessel from the first image data, a reference value region setting means for setting a given region in an image acquired by the electronic endoscope as reference value region, a reference value blood vessel information calculating means for calculating a reference value for the blood vessel information based on second image data for a region within a reference value region set by the reference value region setting means to acquire a reference value blood vessel information, a relative value blood vessel information calculating means for calculating relative value blood vessel information from a difference between the blood vessel information and the reference value blood vessel information, an image producing means for producing a relative value blood vessel information image representing a relative value of the blood vessel information in simulated color from the relative value of blood vessel information, and an image displaying means for displaying a relative value blood vessel information image produced by the image producing means.

In order to attain the above objects, the invention provides a pathological microscope device comprising an illuminating means for illuminating a subject tissue located in a body cavity and containing a blood vessel with illumination light, an observing means including an image sensor for receiving reflected light of the illumination light emitted from the illuminating means to the subject tissue, acquiring an image of the subject tissue, and outputting an imaging signal representing a luminance of the reflected light, a first image data producing means for outputting a plurality of first image data having different wavelength bands from the imaging signal, a blood vessel information producing means for producing blood vessel information on the blood vessel from the first image data, a reference value region setting means for setting a given region in an image acquired by the electronic endoscope as reference value region, a reference value blood vessel information calculating means for calculating a reference value for the blood vessel information based on second image data for a region within a reference value region set by the reference value region setting means to acquire a reference value blood vessel information, a relative value blood vessel information calculating means for calculating relative value blood vessel information from a difference between the blood vessel information and the reference value blood vessel information, an image producing means for producing a relative value blood vessel information image representing a relative value of the blood vessel information in simulated color from the relative value blood vessel information, and an image displaying means for displaying a relative value blood vessel information image produced by the image producing means.

The present invention enables acquisition of a distribution image having an improved robustness of blood vessel information by calculating blood vessel information as a relative value for the whole region with respect to a reference given by a value of blood vessel information for a reference value region.

BRIEF DESCRIPTION OF DRAWINGS

FIG. 8 shows image views illustrating an example of a screen given by a monitor for displaying either an absolute value oxygen saturation level image or a relative value oxygen saturation level image.

FIG. 9 shows image views illustrating an example of a screen given by a monitor for simultaneously displaying both an absolute value oxygen saturation level image and a relative value oxygen saturation level image.

DETAILED DESCRIPTION OF INVENTION

The electronic endoscope system of the invention will be described in detail below based on preferred embodiments illustrated in the attached drawings.

Figure 1:
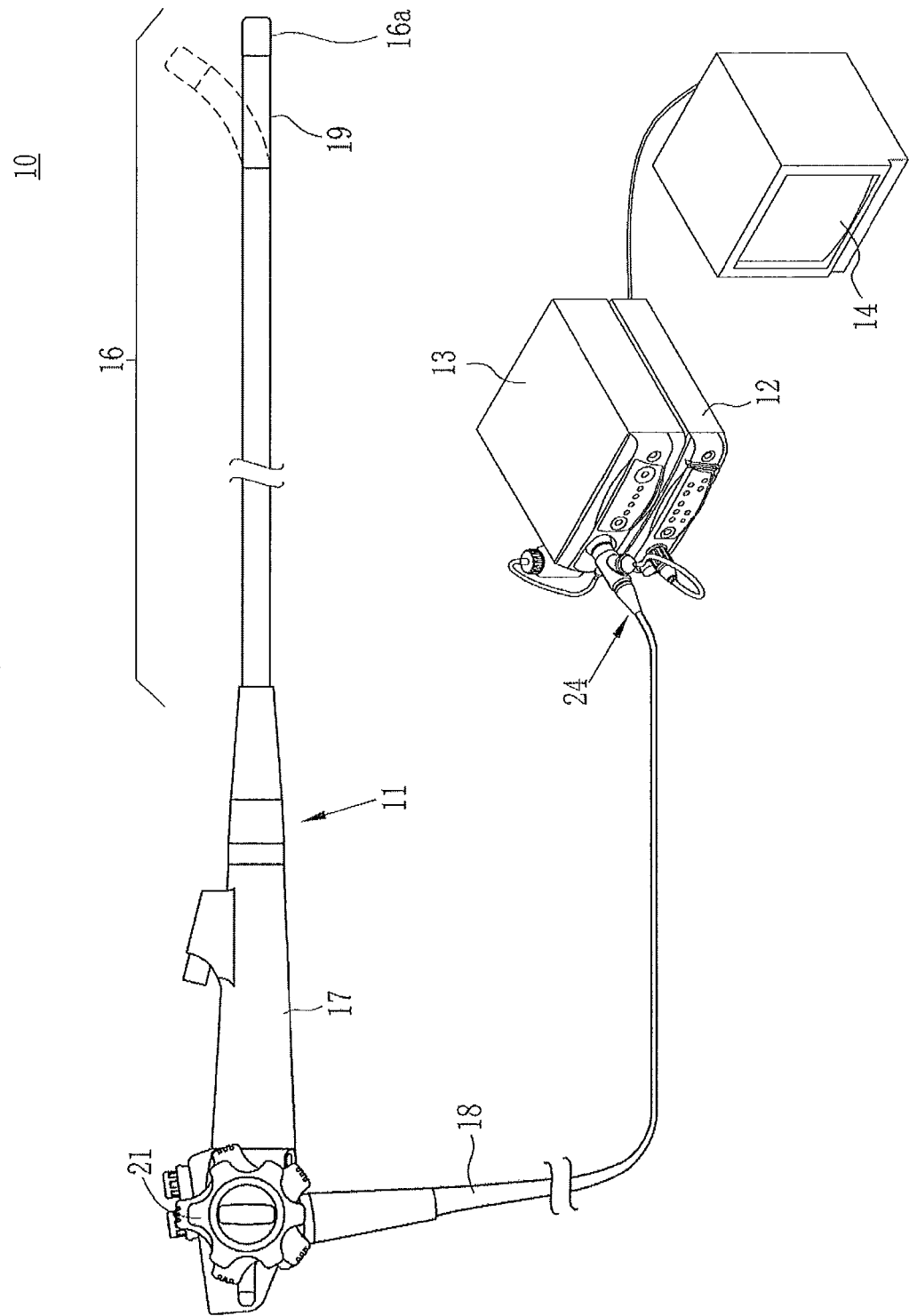
FIG. 1 is an external view of an electronic endoscope system according to a first embodiment of the invention.

FIG. 1 is an external view of a configuration of the electronic endoscope system according to a first embodiment of the invention.

As illustrated in FIG. 1, an electronic endoscope system 10 according to the first embodiment of the invention comprises an electronic endoscope 11 for imaging the inside of a subject's body cavity, a processor 12 for producing an image of a subject tissue in the body cavity based on a signal acquired by imaging, a light source device 13 for supplying light for illuminating the inside of the body cavity, and a monitor 14 for displaying the image of the inside of the body cavity.

The electronic endoscope 11 comprises a flexible insertion section 16 that is inserted into a body cavity, an operating section 17 provided at the base of the insertion section 16, and a universal cord 18 for connecting the operating section 17 to the processor 12 and the light source device 13.

The insertion section 16 has a bending portion 19 at the tip thereof comprising connected bending pieces. The bending portion 19 bends up and down, left and right in response to the operation of an angle knob 21 of the operating section 17. The bending portion 19 has at its tip an end portion 16a incorporating an optical system and other components for imaging the inside of a body cavity. The end portion 16a can be directed in a desired direction in the body cavity according to a bending operation of the bending portion 19.

The universal cord 18 has a connector 24 provided on the side thereof leading to the processor 12 and the light source device 13. The connector 24 is a composite type connector composed of a communication connector and a light source connector and removably connects the electronic endoscope 11 to the processor 12 and the light source device 13.

Figure 2:
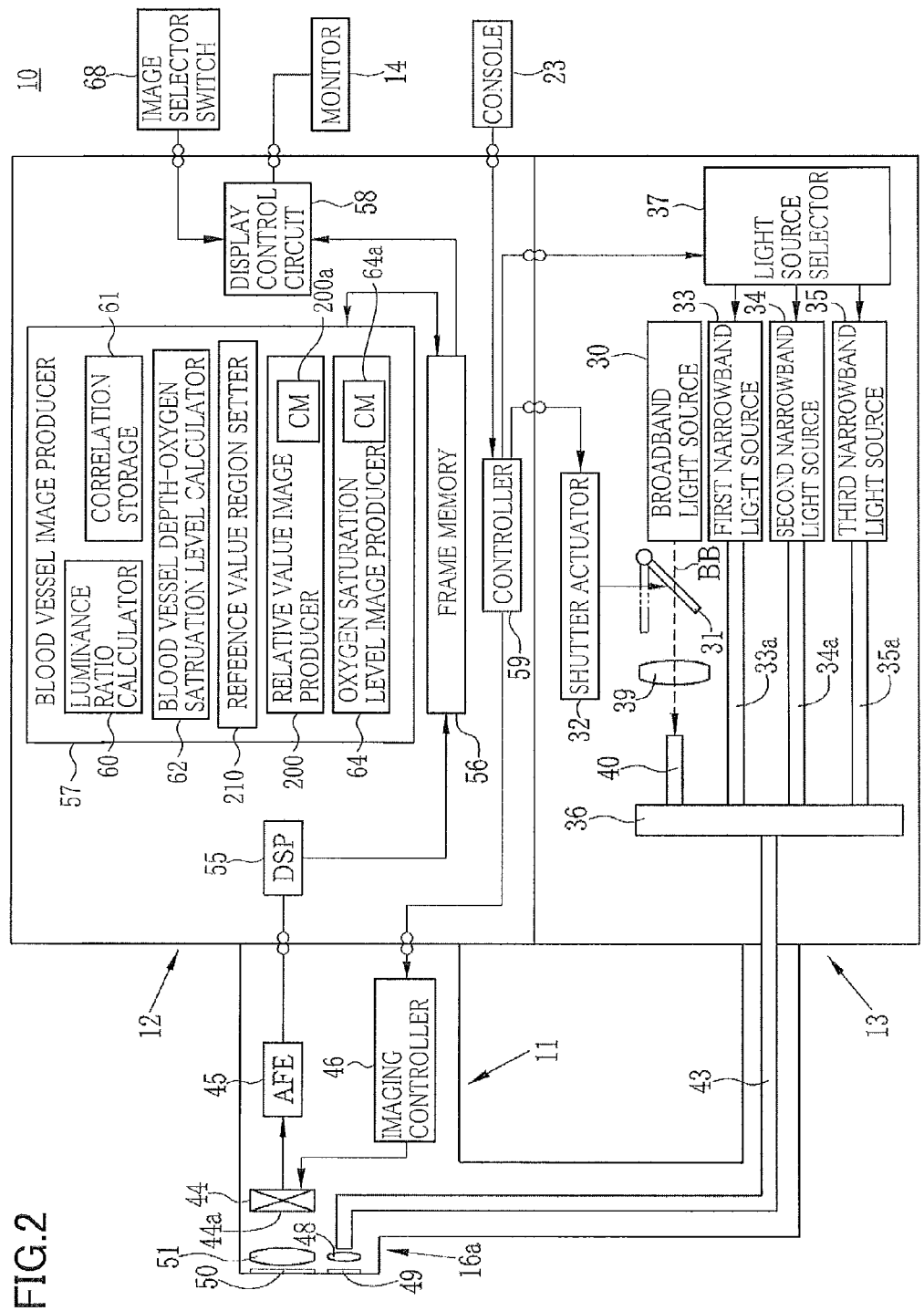
FIG. 2 is a block diagram illustrating an electric configuration of the electronic endoscope system according to the first and a second embodiments of the invention.

As illustrated in FIG. 2, the light source device 13 comprises a broadband light source 30, a shutter 31, a shutter actuator 32, first to third narrowband light sources 33 to 35, a coupler 36, and a light source selector 37.

The broadband light source 30 is a xenon lamp, a white LED, a micro-white (trademark) light source, or the like and produces broadband light BB having a wavelength ranging from a blue region to a red region (about 470 nm to 700 nm). The broadband light source 30 remains lighted at all times when the electronic endoscope 11 is in operation. The broadband light BB emitted from the broadband light source 30 is focused by a condenser lens 39 before entering a broadband optical fiber 40.

The shutter 31 is disposed between the broadband light source 30 and the condenser lens 39 so as to be movable between its inserted position where the shutter 31 is located on the optical path of the broadband light BB to block the broadband light BB and its retracted position where the shutter 31 is retracted from the inserted position to allow the broadband light BB to travel toward the condenser lens 39.

The shutter actuator 32 is connected to a controller 59 in the processor 12 to control the actuation of the shutter 31 according to an instruction from the controller 59.

The first to the third narrowband light sources 33 to 35 are laser diodes or the like. The first narrowband light source 33 produces narrowband light having a wavelength limited to 440 nm+/−10 nm, preferably 445 nm (referred to below as "first narrowband light N1"), the second narrowband light source 34 produces narrowband light having a wavelength limited to 470 nm+/−10 nm, preferably 473 nm (referred to below as "second narrowband light N2"), and the third narrowband light source 35 produces narrowband light having a wavelength limited to 400 nm+/−10 nm, preferably 405 nm (referred to below as "third narrowband light N3"). The first to the third narrowband light sources 33 to 35 are connected respectively to first to third narrowband optical fibers 33a to 35a, allowing the first to the third narrowband light N1 to N3 to enter the first to the third narrowband optical fibers 33a to 35a.

The coupler 36 connects a light guide 43 in the electronic endoscope to the broadband optical fiber 40 and the first to the third narrowband optical fibers 33a to 35a. Thus, the broadband light BB can enter the light guide 43 through the broadband optical fiber 40. The first to the third narrowband light N1 to N3 can enter the light guide 43 through the first to the third narrowband optical fibers 33a to 35a.

The light source selector 37 is connected to the controller 59 in the processor and turns on or off the first to the third narrowband light sources 33 to 35 according to an instruction by the controller 59. In the normal light image mode using the broadband light BB, the inside of a body cavity is illuminated by the broadband light BB to acquire a normal light image while the first to the third narrowband light sources 33 to 35 are turned off. In the special light image mode using the first to the third narrowband light N1 to N3, the illumination of the inside of the body cavity by the broadband light BB is terminated while the first to the third narrowband light sources 33 to 35 are sequentially turned on to acquire special light images.

Specifically, the light source selector 37 first turns on the first narrowband light source 33. Then, imaging of the subject tissue is started with the first narrowband light N1 illuminating the inside of the body cavity. Upon completion of imaging, the controller 59 gives a light source switching instruction to turn off the first narrowband light source 33 and turn on the second narrowband light source 34. Likewise, upon completion of imaging with the second narrowband light N2 illuminating the inside of the body cavity, the second narrowband light source 34 is turned off and the third narrowband light source 35 is turned on. Upon completion of imaging with the third narrowband light N3 illuminating the inside of the body cavity, the third narrowband light source 35 is turned off.

The electronic endoscope 11 comprises the light guide 43, a CCD 44, an analog processor circuit 45 (AFE: analog front end), and an imaging controller 46.

The light guide 43 is a large-diameter optical fiber, a bundle fiber, or the like having its light-receiving end inserted in the coupler 36 in the light source device, whereas its light emitting end is directed toward an illumination lens 48 located in the leading end portion 16a. The light emitted from the light source device 13 is guided through the light guide 43 and then emitted toward the illumination lens 48. The light admitted in the illumination lens 48 is emitted through an illumination window 49 attached to the end face of the leading end portion 16a to illuminate the inside of the cavity. The broadband light BB and the first to the third narrowband light N1 to N3 reflected by the inside of the body cavity pass through an observation window 50 attached to the end face of the leading end portion 16a to enter a condenser lens 51.

The CCD 44 receives the light from the condenser lens 51 with its imaging surface 44a, performs photoelectric conversion of the received light to accumulate a signal charge, and reads out the accumulated signal charge as an imaging signal. The read-out imaging signal is transmitted to an AFE 45. The CCD 44 is a color CCD whose imaging surface 44a has arranged therein three colors of pixels, red (R) pixels, green (G) pixels, and blue (B) pixels, each provided with one of a red filter, a green filter, and a blue filter.

Figure 3:
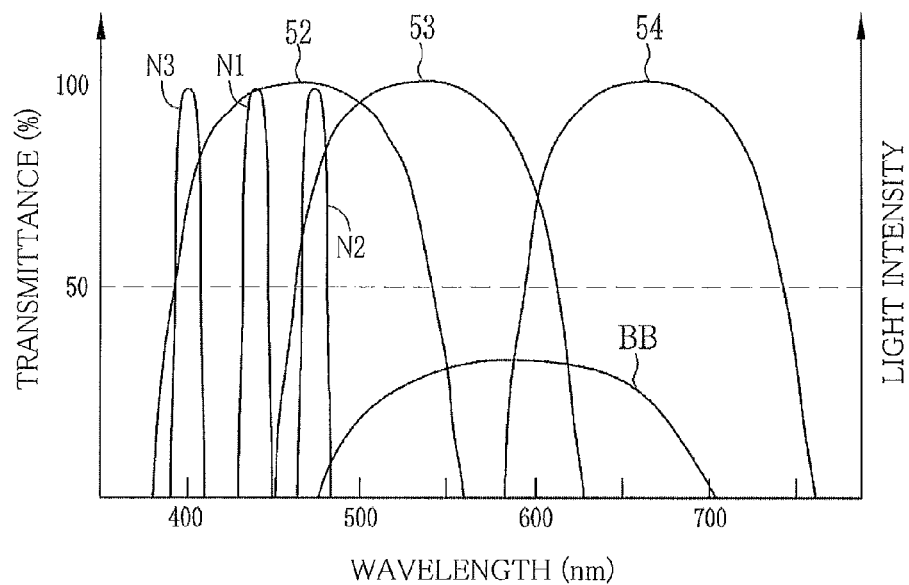
FIG. 3 is a graph illustrating spectral transmittances of red, green, and blue filters.

As illustrated in FIG. 3, the red filters, the green filters, and the blue filters have spectral transmittances 52, 53, and 54, respectively. Among the light entering the condenser lens 51, the broadband light BB has a wavelength ranging from about 470 nm to 700 nm. The red filters, the green filters, and the blue filters pass a wavelength range of broadband light BB corresponding to their spectral transmittances 52, 53 and 54. Now, let imaging signal R be a signal photoelectrically converted by a red pixel, imaging signal G a signal photoelectrically converted by a green pixel, and imaging signal B a signal photoelectrically converted by a blue pixel. Then, the broadband light BB entering the CCD 44 yields a broadband imaging signal composed of the imaging signal R, the imaging signal G, and the imaging signal B.

Among the light entering the condenser lens 51, the first narrowband light N1 has a wavelength of 440 nm+/−10 nm and therefore passes through only the blue filters. Accordingly, the first narrowband light N1 entering the CCD 44 yields a first narrowband imaging signal composed of an imaging signal B. The second narrowband light N2 has a wavelength of 470 nm+/−10 nm and therefore passes through both the blue and green filters. Accordingly, the second narrowband light N2 entering the CCD 44 yields a second narrowband imaging signal composed of an imaging signal B and an imaging signal G. The third narrowband light N3 has a wavelength of 400 nm+/−10 nm and therefore passes through only the blue filters. Accordingly, the first narrowband light N3 entering the CCD 44 yields a third narrowband imaging signal composed of an imaging signal B.

The AFE 45 comprises a correlated double sampling circuit (CDS), an automatic gain control circuit (AGC), and an analog-to-digital converter (A/D) (none of these are shown). The CDS performs correlated double sampling of an imaging signal supplied from the CCD 44 to remove noise generated by actuation of the CCD 44. The AGC amplifies an imaging signal from which noise has been removed by the CDS. The analog-to-digital converter converts an imaging signal amplified by the AGC into a digital imaging signal having a given number of bits, which is applied to the processor 12.

Figure 4A:
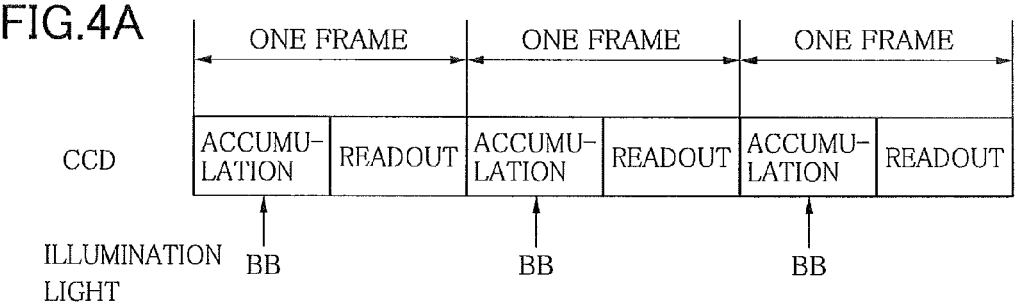
FIG. 4A is a view for explaining operations of a CCD in a normal light image mode.

The imaging controller 46 is connected to the controller 59 in the processor 12 and sends a drive signal to the CCD 44 in response to an instruction given by the controller 59. The CCD 44 outputs an imaging signal to the AFE 45 at a given frame rate according to the drive signal from the imaging controller 46. In the normal light image mode, a total of two operations are performed in one frame of acquisition period as illustrated in FIG. 4A: a step of accumulating a signal charge through photoelectric conversion of the broadband light BB and a step of reading out the accumulated signal charge as a broadband imaging signal. These operations are repeated throughout the normal light image mode.

Figure 4B:
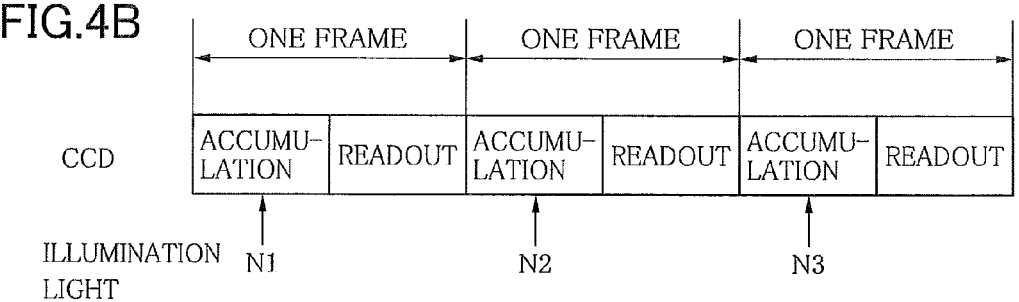
FIG. 4B is a view for explaining operations of a CCD in a special light image mode.

By contrast, when the mode is switched from the normal light image mode to the special light image mode, a total of two operations are first performed in one frame of acquisition period as illustrated in FIG. 4B: a step of accumulating a signal charge through photoelectric conversion of the first narrowband light N1 and a step of reading out the accumulated signal charge as a first narrowband imaging signal. Upon completion of readout of the first narrowband imaging signal, a total of two operations are performed in one frame of acquisition period: a step of accumulating a signal charge through photoelectric conversion of the second narrowband light N2 and a step of reading out the accumulated signal charge as a second narrowband imaging signal. Upon completion of readout of the second narrowband imaging signal, a total of two operations are performed in one frame of acquisition period: a step of accumulating a signal charge through photoelectric conversion of the third narrowband light N3 and a step of reading out the accumulated signal charge as a third narrowband imaging signal.

As illustrated in FIG. 2, the processor 12 comprises a digital signal processor 55 (DSP), a frame memory 56, a blood vessel image producer 57, and a display control circuit 58, all of these components being controlled by the controller 59.

The DSP 55 performs color separation, color interpolation, white balance adjustment, gamma correction, and the like of the broadband imaging signal and the first to the third narrowband imaging signals outputted from AFE 45 in the electronic endoscope to produce broadband image data and the first to the third narrowband image data (first image data). Thus, the DSP 55 is a first image data producing means.

The frame memory 56 stores the broadband image data and the first to the third narrowband image data produced by the DSP 55. The broadband image data is color image data containing colors of red, green, and blue.

The blood vessel image producer 57 comprises a luminance ratio calculator 60, a correlation storage 61, a blood vessel depth-oxygen saturation level calculator 62, an oxygen saturation level image producer 64, a relative value image producer 200, and a reference value region setter 210.

The luminance ratio calculator 60 determines a blood vessel region containing a blood vessel from the first to the third narrowband image data stored in the frame memory 56. The luminance ratio calculator 60 obtains a first luminance ratio S1/S3 between the first and the third narrowband image data and a second luminance ratio S2/S3 between the second and the third narrowband image data corresponding to a pixel at the same position in the blood vessel region. S1 is a luminance of a pixel of the first narrowband image data, S2 a luminance of a pixel of the second narrowband image data, and S3 a luminance of a pixel of the third narrowband image data. The blood vessel region may be determined, for example, by a method whereby the blood vessel region is obtained from the difference between the luminance of a blood vessel region of interest and the luminance of the other region.

Figure 5:
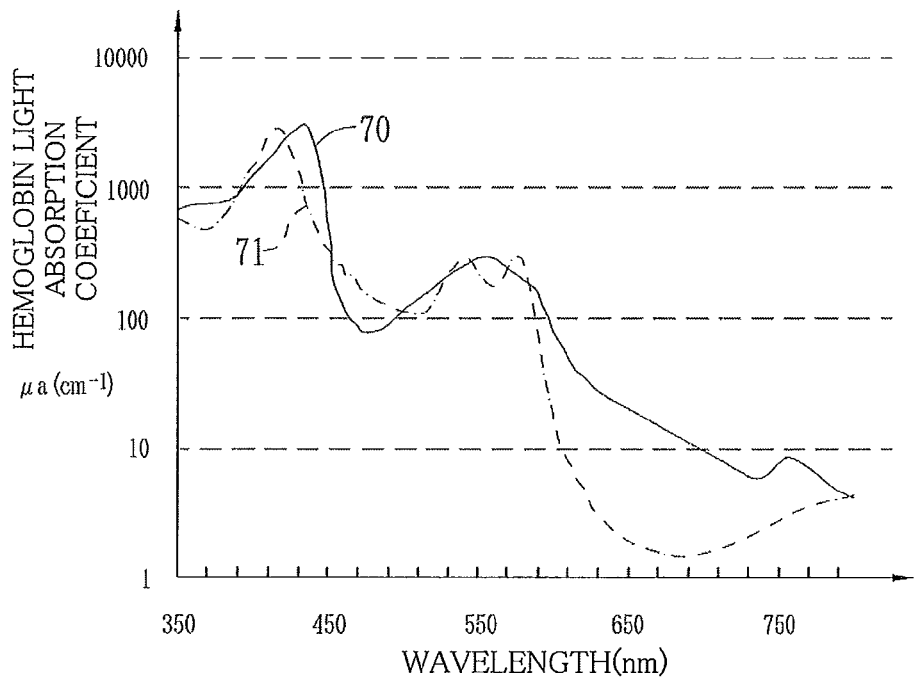
FIG. 5 is a graph illustrating an absorption coefficient of hemoglobin.

The correlation storage 61 stores a correlation between the first and the second luminance ratios S1/S3 and S2/S3 on the one hand and an oxygen saturation level in a blood vessel and a blood vessel depth on the other hand. That correlation is one where a blood vessel contains hemoglobin exhibiting light absorption coefficients as shown in FIG. 5 and is obtained by analyzing, for example, a number of the first to the third narrowband image data accumulated through diagnoses or the like hitherto made. As illustrated in FIG. 5, the hemoglobins in a blood vessel have light absorption characteristics having the light absorption coefficient μa changing according to the wavelength of light used for illumination. The light absorption coefficient μa indicates an absorbance, i.e., a degree of light absorption by hemoglobin, and is a coefficient in an expression $I_0\exp(-\mu a \times x)$ showing the attenuation of light illuminating the hemoglobin. In this expression, Io is the intensity of light emitted from the light source device to illuminate a subject tissue; x (cm) is a depth of a blood vessel inside the subject tissue.

A reduced hemoglobin 70 and an oxygenated hemoglobin 71 have different light absorption characteristics such that they have different absorbances except for the isosbestic point at which both exhibit the same absorbance (intersection of light absorption characteristics curves of hemoglobins 70 and 71 in FIG. 5). With a difference in absorbance, the luminance varies even when the same blood vessel is illuminated by light having the same intensity and the same wavelength. The luminance also varies when the illumination light has the same intensity but varies in wavelength because a difference in wavelength causes the light absorption coefficient pa to change.

In view of the light absorption characteristics of hemoglobin as described above and considering the fact that wavelengths whereby the absorbance varies according to the oxygen saturation level lie in a range of 445 nm and 405 nm and that light having a short wavelength and hence having a short reaching depth is required in order to retrieve blood vessel depth information, at least one of the first to the third narrowband light N1 to N3 preferably has a wavelength range whose central wavelength is 450 nm or less. According to the first and the second embodiment of the invention, the first and the third narrowband light are such narrowband light. Further, with the same oxygen saturation level, a difference in wavelength causes a difference in absorption coefficient and also a difference in reaching depth into a mucus membrane. Therefore, using the property of light whose reaching depth varies with the wavelength permits obtaining correlation between luminance ratio and blood vessel depth.

Figure 6:
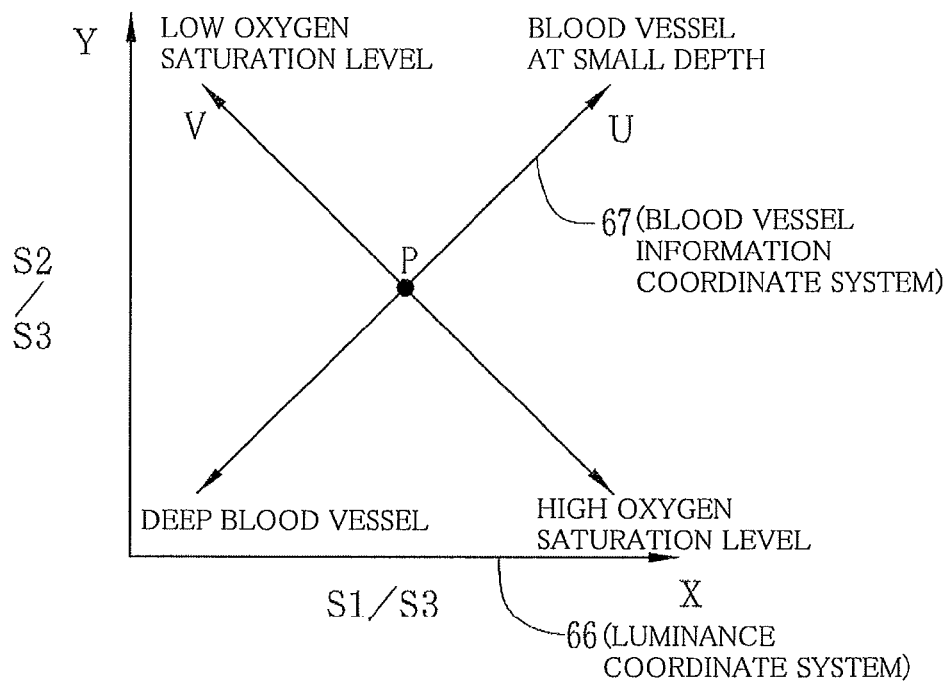
FIG. 6 is a graph illustrating a correlation between first and second luminance ratios S1/S3 and S2/S3 on the one hand and blood vessel depth and oxygen saturation level on the other hand.

As illustrated in FIG. 6, the correlation storage 61 stores a correlation in correspondence between the coordinate points in a luminance coordinate system 66 representing the first and the second luminance ratios S1/S3 and S2/S3 and the coordinate points in a blood vessel information coordinate system 67 representing oxygen saturation level and blood vessel depth. The luminance coordinate system 66 is an XY coordinate system, where the X axis shows the first luminance ratio S1/S3 and the Y axis shows the second luminance ratio S2/S3. The blood vessel information coordinate system 67 is a UV coordinate system provided on the luminance coordinate system 66, where the U axis shows the blood vessel depth and the V axis shows the oxygen saturation level. Because the blood vessel depth has a positive correlation with the luminance coordinate system 66, the U axis has a positive slope. The U axis shows that a blood vessel of interest is located at an increasingly smaller depth as a position on the U axis moves obliquely up rightward and that a blood vessel of interest is located at an increasingly greater depth as a position on the U axis moves obliquely down leftward. On the other hand, because the oxygen saturation level has a negative correlation with the luminance coordinate system 66, the V axis has a negative slope. The V axis shows that the oxygen saturation level is lower as a position on the V axis moves obliquely up leftward and that the oxygen saturation level is higher as a position on the V axis moves obliquely down rightward.

In the blood vessel information coordinate system 67, the U axis and the V axis cross each other at right angles at an intersection P. This is because the magnitude of absorbance reverses between illumination by the first narrowband light N1 and illumination by the second narrowband light N2. More specifically, as illustrated in FIG. 5, illumination by the first narrowband light N1 having a wavelength of 440 nm+/−10 nm allows the light absorption coefficient of the reduced hemoglobin 70 to be greater than the light absorption coefficient of the oxygenated hemoglobin 71 having a high oxygen saturation level whereas illumination by the second narrowband light N2 having a wavelength of 470 nm+/−10 nm allows the light absorption coefficient of the oxygenated hemoglobin 71 to be greater than the light absorption coefficient of the reduced hemoglobin 70 having a high oxygen saturation level, thus causing the magnitude of the absorbance to reverse. When narrowband light permitting no absorbance reversal are used in lieu of the first to the third narrowband light N1 to N3, the U axis and the V axis do not cross each other at right angles. With illumination provided by the third narrowband light N3 having a wavelength of 400 nm+/−10 nm, the oxygenated hemoglobin and the reduced hemoglobin have a substantially equal light absorption coefficient.

The blood vessel depth-oxygen saturation level calculator 62 determines an oxygen saturation level and a blood vessel depth corresponding to the first and the second luminance ratios S1/S3 and S2/S3 calculated by the luminance ratio calculator 60 based on the correlation stored in the correlation storage 61. Now, in the first and the second luminance ratios S1/S3 and S2/S3 calculated by the luminance ratio calculator 60, let S1\*/S3\* and S2\*/S3\* be the first luminance ratio and the second luminance ratio respectively for a given pixel in the blood vessel region.

Figure 7A:
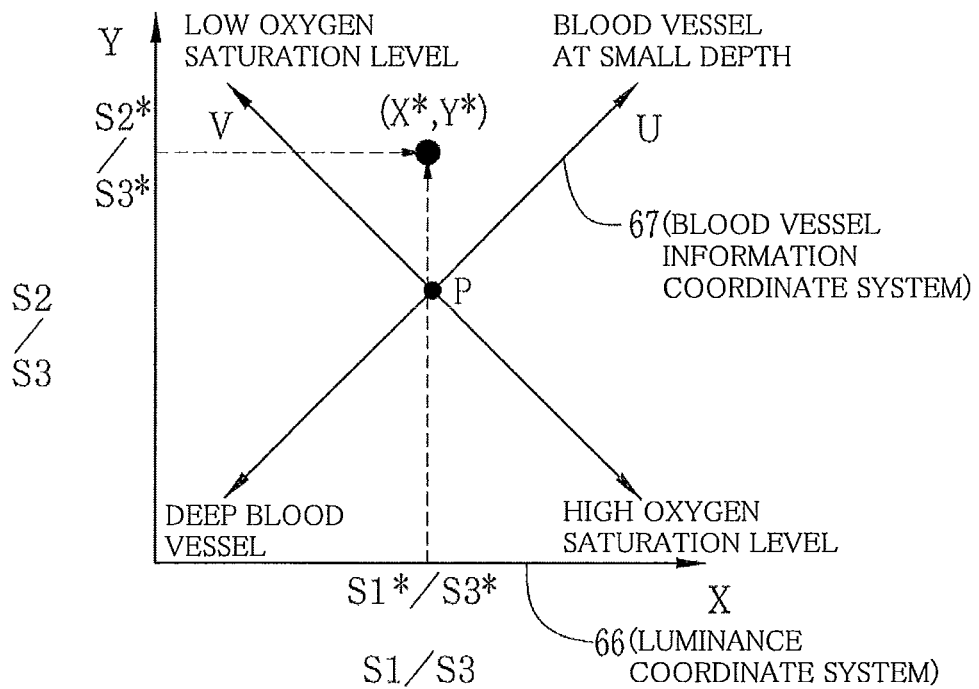
FIG. 7A is a view for explaining how a coordinate point (X*, Y*) in a luminance coordinate system is obtained from first and second luminance ratios S1*/S3* and S2*/S3*.
Figure 7B:
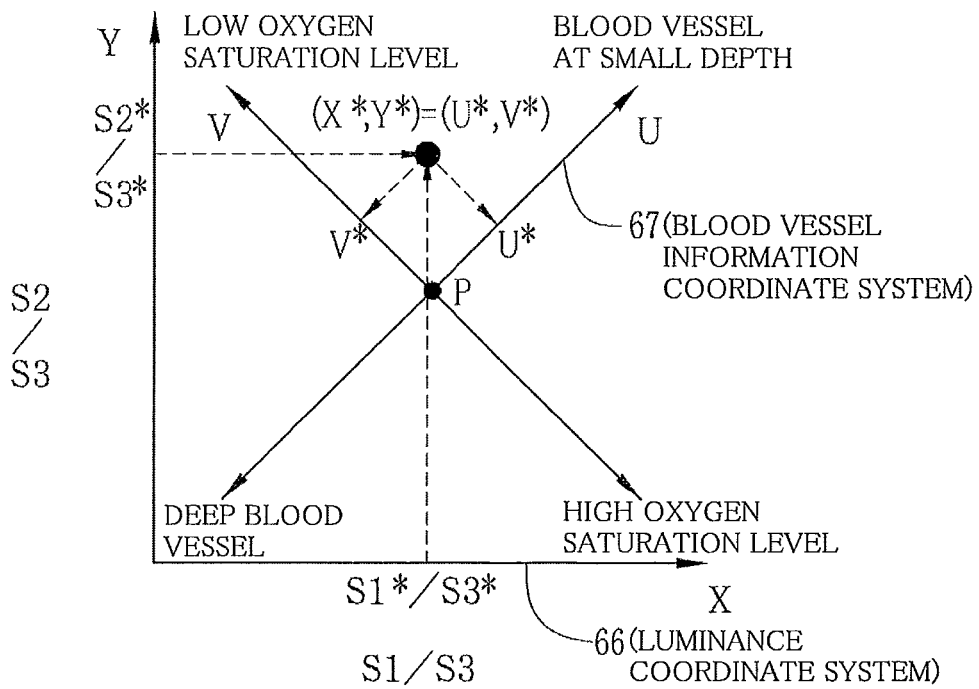
FIG. 7B is a view for explaining how a coordinate point (U*, V*) in a blood vessel information coordinate system corresponding to the coordinate point (X*, Y*) is obtained.

As illustrated in FIG. 7A, the blood vessel depth-oxygen saturation level calculator 62 determines a coordinate point (X\*, Y\*) corresponding to the first and the second luminance ratios S1\*/S3\* and S2\*/S3\* in the luminance coordinate system 66. Upon the coordinate point (X\*, Y\*) being determined, the blood vessel depth-oxygen saturation level calculator 62 determines a coordinate point (U\*, V\*) corresponding to the coordinate point (X\*, Y\*) in the blood vessel information coordinate system 67 as illustrated in FIG. 7B. Thus, blood vessel depth information U\* and oxygen saturation level information V\* are obtained for a given pixel in the blood region. The blood vessel depth information U\* and the oxygen saturation level information V\* are reference value blood vessel depth information Uav\* and reference value oxygen saturation level information Vav\* when reference values are to be obtained; the blood vessel depth information U\* and the oxygen saturation level information V\* are absolute blood vessel depth information Uab\* and absolute value oxygen saturation level information Vab\* when absolute values are to be obtained.

The blood vessel depth-oxygen saturation level calculator 62 obtains the reference value blood vessel depth information Uav\* and the reference value oxygen saturation level information Vav\* for a reference value region set by a reference value region setter 210 described later and obtains the absolute blood vessel depth information Uab\* and the absolute value oxygen saturation level information Vab\* for the whole imaged blood vessel region. Thus, the luminance ratio calculator 60, the correlation storage 61, and the blood vessel depth-oxygen saturation level calculator 62 are blood vessel information producing means and reference value blood vessel information calculating means.

The blood vessel depth information is used to determine whether a blood vessel region of interest is a superficial-layer blood vessel region (micro-blood vessel region) or a non-superficial-layer blood vessel region (intermediate-layer blood vessel, deep-layer blood vessel) in a second embodiment.

The reference value region setter 210 sets a reference value region for obtaining the reference value blood vessel depth information Uav\* and the reference value oxygen saturation level information Vav\*. The reference value region is a region for calculating a reference value for obtaining relative value blood vessel information (oxygen saturation level information, blood level information). The reference value region may be entered from a console 23 using a pointing device such as a mouse. Alternatively, in order to specify a region other than the superficial-layer blood vessel region (micro-blood vessel) as the reference value region, a region having the absolute blood vessel depth information Uab\* indicating an intermediate-layer blood vessel (diameter of about 20 μm to 100 μm) or a deep-layer blood vessel (diameter of about 100 μm or more) may be automatically specified as the reference value region. Image data of a region set as reference value region will be called second image data.

The oxygen saturation level image producer 64 has a color map 64a (CM) where color information is assigned according to the level of the oxygen saturation levels. More specifically, the color map 64a permits easy distinction of oxygen saturation level by color assignment such that, for example, a low oxygen saturation level is assigned a color of cyan, a medium oxygen saturation level is assigned a color of magenta, and a high oxygen saturation level is assigned a color of yellow. From the color map 64a, the oxygen saturation level image producer 64 determines color information corresponding to the absolute value oxygen saturation level information Vab\* calculated by the blood vessel depth-oxygen saturation level calculator 62.

When all the pixels in the blood vessel region have been assigned color information, the oxygen saturation level image producer 64 reads out broadband image data from the frame memory 56 and incorporates color information in the read-out broadband image data. Thus, the absolute value oxygen saturation level image data incorporating absolute value oxygen saturation level information is produced. The absolute value oxygen saturation level image data thus produced is stored again in the frame memory 56. The color information may be incorporated in one of the first to the third narrowband image data or in a synthesized image obtained by combining these in lieu of the broadband image data.

The relative value image producer 200 has a color map 200a (CM) where color information is assigned according to the level of the oxygen saturation levels. More specifically, the color map 200a permits easy distinction of oxygen saturation level according to the relative value thereof such that, for example, an oxygen saturation level lower than the reference value is assigned a color of blue, an oxygen saturation level equal to the reference value is assigned a color of yellow, and an oxygen saturation level higher than the reference level is assigned a color of red.

The relative value image producer 200 is a relative value blood vessel information calculating means for obtaining relative value oxygen saturation level information Vr*, a difference between the absolute value oxygen saturation level information Vab* and the reference value oxygen saturation level information Vav* calculated by the blood vessel depth-oxygen saturation level calculator 62.

Similarly to the oxygen saturation level image producer 64, the relative value image producer 200 determines color information corresponding to the relative value oxygen saturation level information Vr* from the color map 200a. Then, the relative value image producer 200 incorporates this color information in the broadband image data to produce the relative value oxygen saturation level image data. Thus, the relative value image producer 200 is an image producing means.

Like the absolute value oxygen saturation level image data, the relative value oxygen saturation level image data thus produced is stored in the frame memory 56.

The display control circuit 58 reads out one or more images from the frame memory 56 and allows the monitor 14 to display the read-out image or images. The images may be displayed in various modes. As illustrated in FIG. 8, for example, the monitor 14 may display a broadband image 72 on one side and an absolute value oxygen saturation level image 73 or the relative value oxygen saturation level image 74 selected by an image selector switch 68 (see FIG. 2) on the other side. In the absolute value oxygen saturation level image 73 illustrated in FIG. 8, a blood vessel image 75 is shown in cyan indicating a lower oxygen saturation level, a blood vessel image 76 is shown in magenta indicating a medium oxygen saturation level, and a blood vessel image 77 is shown in yellow indicating a higher oxygen saturation level. In the relative value oxygen saturation level image 74, a blood vessel image 80 is shown in cyan indicating an oxygen saturation level lower than a reference value, a blood vessel image 81 is shown in magenta indicating an oxygen saturation level equal to the reference value, and a blood vessel image 82 is shown in yellow indicating an oxygen saturation level higher than the reference value.

Figure 10:
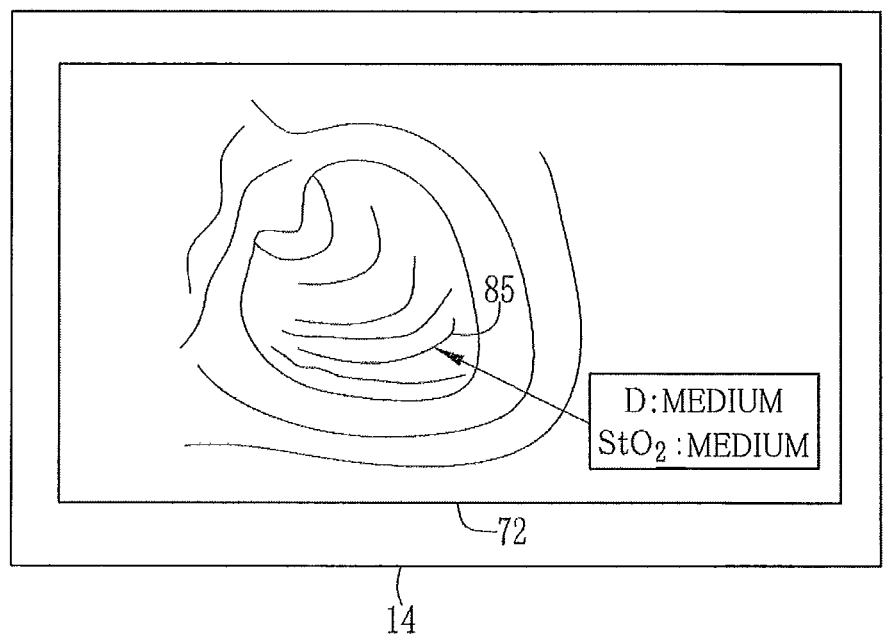
FIG. 10 is an image view illustrating an example of a screen of a monitor where blood vessel information, i.e., blood vessel depth information and absolute value oxygen saturation level information, are given in textual information together with an image.

As illustrated in FIG. 9, the absolute value oxygen saturation level image 73 and the relative value oxygen saturation level image 74 may be both displayed simultaneously with the display mode shown in FIG. 8. As illustrated in FIG. 10, in lieu of displaying the absolute value oxygen saturation level image 73 and the relative value oxygen saturation level image 74, a given blood vessel image 85 in the broadband image 72 may be specified, with the oxygen saturation level ($StO_2$ (saturated oxygen)) of the blood vessel image 85 given in textual information.

Figure 11:
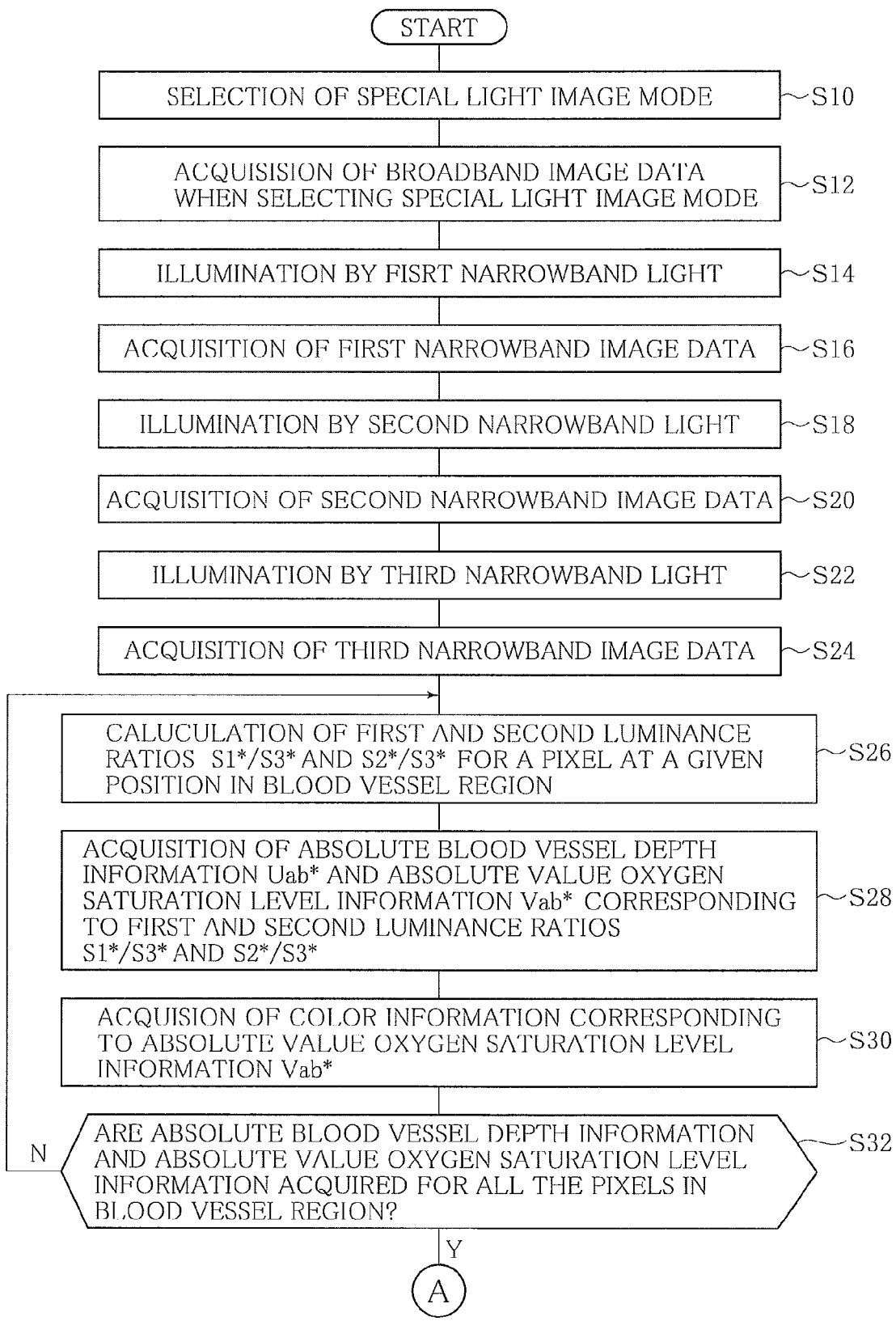
FIG. 11 is a flow chart illustrating a procedure of calculating absolute value, reference value, and relative value oxygen saturation level information and a procedure of producing absolute value and relative value oxygen saturation level images incorporating such information.
Figure 12:
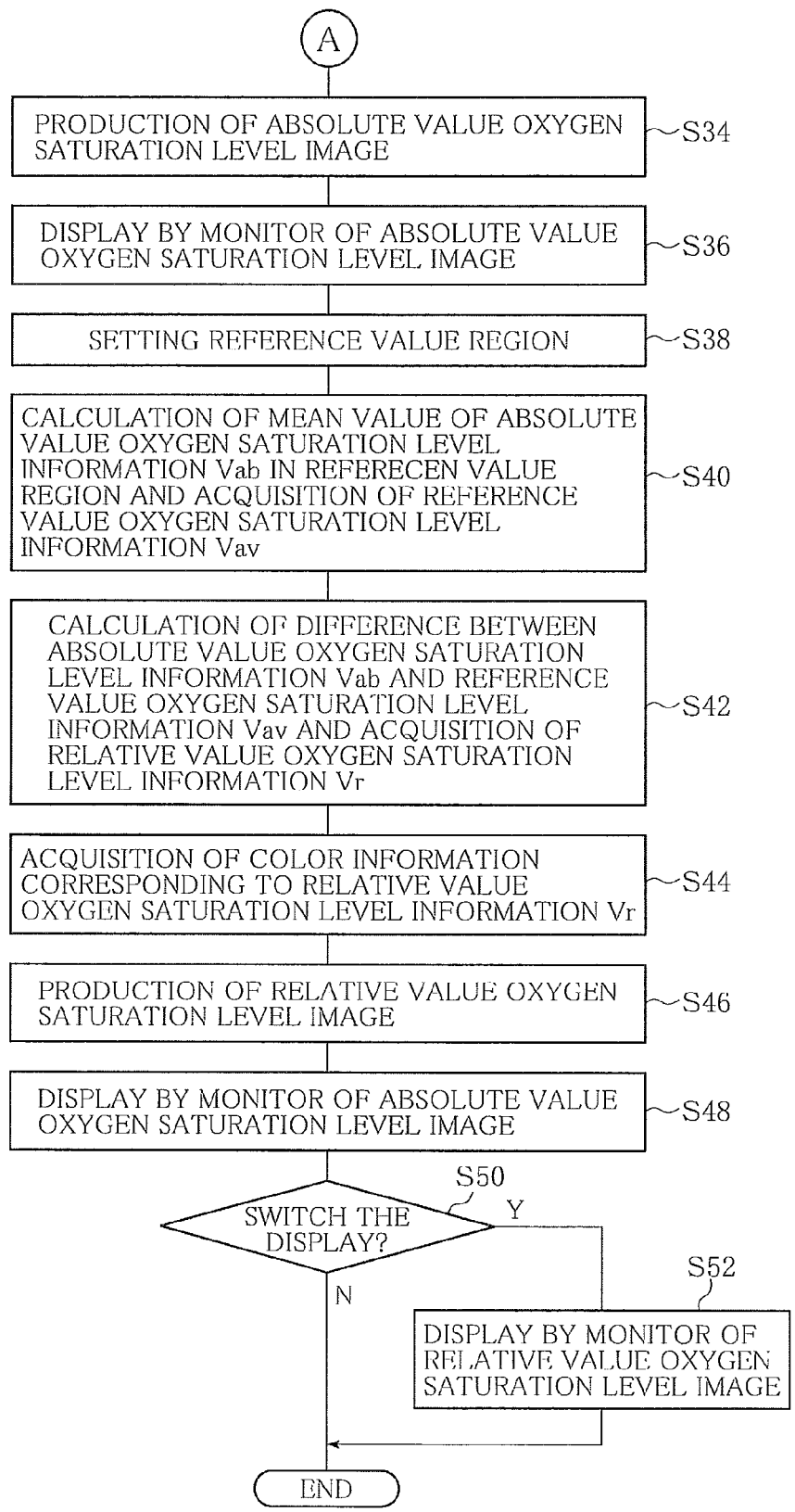
FIG. 12 is a flow chart following the flow of FIG. 11.

Next, we will describe a procedure of calculating the blood vessel depth-oxygen saturation level information and a procedure of producing the absolute value oxygen saturation level image and the relative value oxygen saturation level image incorporating such information referring to the flowchart illustrated in FIGS. 11 and 12.

First, an operator uses the console 23 to perform a freeze operation for acquiring a still image while the normal light image mode is switched to the special light image mode (step S10). When the mode is switched to the special light image mode, the broadband image data as of the time the special light image mode is selected is stored in the frame memory 56 as image data used to produce the oxygen saturation level image (step S12). The broadband image data used to produce the oxygen saturation level image or the like may be broadband image data obtained before operating the console.

Upon receiving an illumination stop signal from the controller 59, the shutter actuator 32 moves the shutter 31 from the retracted position to the inserted position, causing the broadband light BB to stop illuminating the inside of the body cavity. When illumination by the broadband light BB is stopped, the controller 59 sends the light source selector 37 an illumination start instruction. Thereupon, the light source selector 37 turns on the first narrowband light source 33 to illuminate the inside of the body cavity with the first narrowband light N1 (step S14). Upon the narrowband light N1 illuminating the inside of the body cavity, the controller 59 sends the imaging controller 46 an imaging instruction. Thus, imaging is done by illumination with the first narrowband light N1, and the first narrowband imaging signal obtained by the imaging is sent through the AFE 45 to the DSP 55. The DSP 55 produces the first narrowband image data based on the first narrowband imaging signal. The first narrowband image data thus produced is stored in the frame memory 56 (step S16).

When the first narrowband image data has been stored in the frame memory 56, the light source selector 37 switches the light for illuminating the inside of the body cavity from the first narrowband light N1 to the second narrowband light N2 in response to the light source switching instruction from the controller 59 (step S18). Then, imaging is done similarly to the case using the first narrowband light N1 to produce the second narrowband image data based on the second narrowband imaging signal obtained by the imaging. The second narrowband image data thus produced is stored in the frame memory 56 (step S20).

When the second narrowband image data has been stored in the frame memory 56, the light source selector 37 switches the light for illuminating the inside of the body cavity from the second narrowband light N2 to the third narrowband light N3 in response to the light source switching instruction from the controller 59 (step S22). Then, imaging is done similarly to the cases using the first and the second narrowband light N1, N2 to produce the third narrowband image data based on the third narrowband imaging signal obtained by the imaging. The third narrowband image data thus produced is stored in the frame memory 56 (step S24). Thus, image data obtained by illumination with the individual wavelengths are acquired by the frame sequential method.

When the broadband image data and the first to the third narrowband image data have been stored in the frame memory 56, the luminance ratio calculator 60 determines the blood vessel region containing a blood vessel from three image data, i.e., the first narrowband image data, the second narrowband image data, and the third narrowband image data. Then, the luminance ratio calculator 60 calculates the first luminance ratio S1*/S3* between the first and the third narrowband image data and the second luminance ratio S2*/S3* between the second and the third narrowband image data corresponding to a pixel at the same position in the blood vessel region (step S26).

Next, the blood vessel depth-oxygen saturation level calculator 62 determines the coordinate point (X*, Y*) in the luminance coordinate system corresponding to the first and the second luminance ratios S1*/S3* and S2*/S3* based on the correlation stored in the correlation storage 61. Further, the coordinate point (U*, V*) in the blood vessel information coordinate system corresponding to the coordinate point (X*, Y*) is determined to obtain the absolute value blood vessel depth information Uab* and the absolute value oxygen saturation level information Vab* for a given pixel in the blood vessel region (step S28).

When the absolute value oxygen saturation level information Vab* has been obtained, color information corresponding to the absolute value oxygen saturation level information Vab* is determined from the CM 64a in the oxygen saturation level image producer 64. The color information thus determined is stored in a RAM (not shown) in the processor 12 (step S30).

Upon storage of the color information in the RAM, the above procedure is followed to obtain the absolute value blood vessel depth information Uab* and the absolute value oxygen saturation level information Vab* corresponding to all the pixels in the blood vessel region and determine color information corresponding to the absolute value oxygen saturation level information Vab* (step S32).

Then, when the color information corresponding to the absolute value oxygen saturation level information for all the pixels in the blood vessel region have been obtained, the oxygen saturation level image producer 64 reads out the broadband image data from the frame memory 56 and incorporates the color information stored in the RAM in the broadband image data to produce the absolute value oxygen saturation level image data, which is a simulated color image. The absolute value oxygen saturation level image data thus produced is stored again in the frame memory 56 (step S34).

The display control circuit 58 reads out the broadband image data and the absolute value oxygen saturation level image data from the frame memory 56 and displays the absolute value oxygen saturation level image on the monitor 14 based on these read-out image data (step S36).

The reference value region setter 210 causes the monitor 14 to display, for example, a message, so that the operator may set a reference value region for calculating a reference value of the oxygen saturation level using a pointing device (e.g. a mouse) on the console 23. Next, the operator operates the pointing device to set the reference value region (step S38). The reference value region may for example be a region of non-lesion area. Setting the reference value region may be made possible at any time after the absolute value oxygen saturation level image is displayed without the need to display a message, etc.

When the reference value region has been set, the relative value image producer 200 calculates a mean value of the absolute value oxygen saturation level information Vab of the image data (second image data) in the reference value region as set by the reference value region setter 210 and produces the reference value oxygen saturation level information Vav (step S40). The relative value image producer 200 calculates the difference between the absolute value oxygen saturation level information Vab and the reference value oxygen saturation level information Vav for all the pixels in the blood vessel region and produces the relative value oxygen saturation level information Vr for all the pixels in the blood vessel region (step S42).

Upon production of the relative value oxygen saturation level information Vr, a CM 200a in the relative value image producer 200 determines the color information corresponding to the relative value oxygen saturation level information Vr for all the pixels in the blood vessel region. The color information thus determined is stored in the RAM (not shown) in the processor 12 (step S44).

Then, the relative value image producer 200 reads out the broadband image data from the frame memory 56 and incorporates the color information stored in the RAM in the broadband image data to produce the relative value oxygen saturation level image data, which is a simulated color image. The relative value oxygen saturation level image data thus produced is stored again in the frame memory 56 (step S46).

The display control circuit 58 reads out the broadband image data, the absolute value oxygen saturation level image data, and the relative value oxygen saturation level image from the frame memory 56 and displays the broadband image 72, the absolute value oxygen saturation level image 73, and the relative value oxygen saturation level image 74 as illustrated in FIG. 8 on the monitor 14 based on the read-out image data (step S48). The monitor 14 illustrated in FIG. 8 displays the broadband image 72, which is a normal light image, and the absolute value oxygen saturation level image 73 simultaneously in juxtaposition. When the image selector switch 68 switches the screen images (step S50), the monitor 14 displays the broadband image 72, which is a normal light image, and the relative value oxygen saturation level image 74 simultaneously in juxtaposition (step S52). The operator may switch between the absolute value oxygen saturation level image 73 and the relative value oxygen saturation level image 74 as he/she desires. Alternatively, the three images, i.e., the broadband image 72, the absolute value oxygen saturation level image 73, and the relative value oxygen saturation level image 74 may all be simultaneously displayed on the monitor 14 as illustrated in FIG. 9.

As compared with the electronic endoscope system according to the above first embodiment of the invention illustrated in FIG. 2, the second embodiment uses the absolute value blood vessel depth information to determine whether a blood vessel region of interest is a superficial-layer blood vessel region (micro-blood vessel region) or a non-superficial-layer blood vessel region (intermediate-layer blood vessel or deep-layer blood vessel) for all the pixels in the blood vessel region and automatically uses the non-superficial-layer blood vessel region as a reference value region. The second embodiment basically has the same configuration as the first embodiment. Thus, like components are given like reference characters, and drawings and detailed descriptions thereof will be omitted.

The electronic endoscope system according to the second embodiment operates similarly to the electronic endoscope system according to the first embodiment. Thus, redundant descriptions will not be made below, focusing on unshared features, which are the steps S10 and S38 in the flowchart illustrated in FIGS. 11 and 12.

According to the second embodiment of the invention, when the operator selects the special light image mode at the console 23 in the step S10, this automatically starts the freeze operation (still image) or, where a moving image is outputted, the output of the CCD 44 sequentially undergoes real-time processing.

In the step S38, the reference value region setter 210 uses the absolute value blood vessel depth information for all the pixels in the blood vessel region acquired in the step S32 to determine whether a blood vessel region of interest is a superficial-layer blood vessel region (micro-blood vessel region) or a non-superficial-layer blood vessel region (intermediate-layer blood vessel or deep-layer blood vessel), and automatically designates the non-superficial-layer blood vessel region as the reference value region. The reference value region may be the whole non-superficial-layer blood vessel region or a given position in the non-superficial-layer blood vessel region or a region therein having a given size.

Whether or not a pixel of interest is a superficial-layer blood vessel region may be determined using an image signal ratio between two images acquired by illumination with light having wavelengths of 405 nm and 473 nm, respectively. More specifically, when a blood vessel of interest is a superficial-layer minuteness blood vessel, its pixel value ratio S(405)/S(473) tends to be small. Therefore, selecting a region having a great pixel value ratio through a threshold processing allows identification of a non-superficial-layer blood vessel region (intermediate-layer blood vessel or deep-layer blood vessel). The superficial-layer blood vessel region (micro-blood vessel region) designates a part of a blood vessel located in a digestive tract mucosa surface of interest and having a diameter of about 10 µm to 20 µm. The non-superficial-layer blood vessel region designates a region other than the superficial-layer blood vessel region, i.e., an intermediate-layer blood vessel region and a deep-layer blood vessel region. The intermediate-layer blood vessel has a diameter of about 20 µm to 100 µm; the deep-layer blood vessel has a diameter of about 100 µm or greater.

Thereafter, as in the case of the first embodiment, the reference value oxygen saturation level information is obtained, and the relative value oxygen saturation level information is obtained from the difference between the absolute value oxygen saturation level Information and the reference value oxygen saturation level information to produce the relative value oxygen saturation level image.

As described above, the second embodiment eliminates the need for the operator to set the reference value region by enabling automatic designation of the non-superficial-layer blood vessel region as the reference value region.

Figure 13:
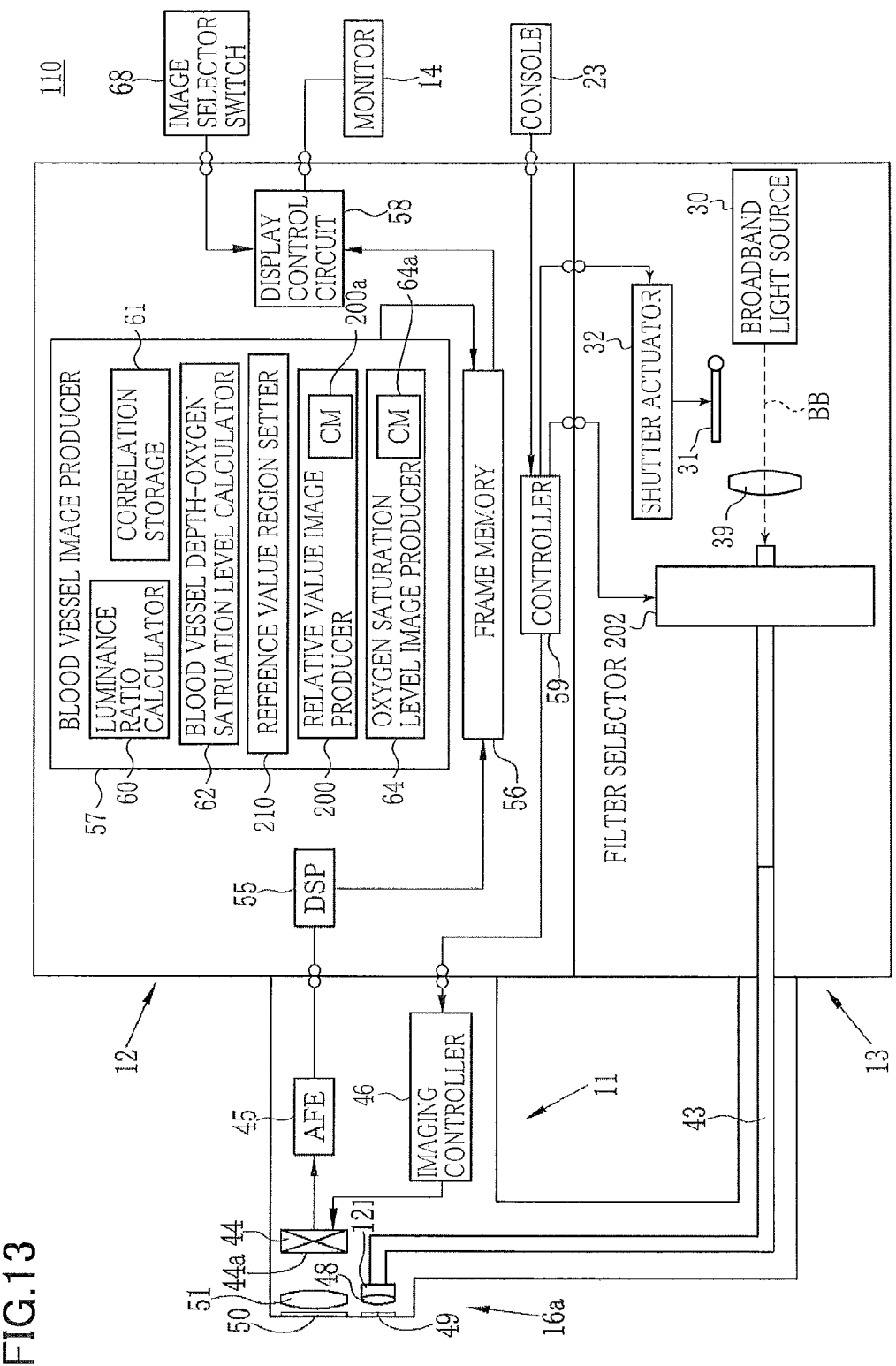
FIG. 13 is a block diagram illustrating an electric configuration of the electronic endoscope system according to a third embodiment of the invention.

FIG. 13 is a block diagram illustrating a configuration of an electronic endoscope system 110, a third embodiment of the invention different from the first and the second embodiments described above.

As compared with the electronic endoscope system according to the second embodiment of the invention illustrated in FIG. 2, the electronic endoscope system 110 uses a broadband light source and an optical filter in the illumination light source to produce three kinds of narrowband light having different wavelengths from those used in the second embodiment but otherwise basically has a similar configuration. Thus, like components are given like reference characters, and detailed descriptions thereof will be omitted.

A filter selector 202 is provided to switch between optical filter regions and receive the broadband light BB emitted from the broadband light source 30 and focused by the condenser lens 39. The filter selector 202 causes the first to the third narrowband light N1 to N3 to be produced by switching between the optical filter and switches between the first to the third narrowband light N1 to N3 and the broadband light BB. The first to the third narrowband light N1 to N3 used in the electronic endoscope system 110 have central wavelengths of 540 nm, 560 nm, and 500 nm, respectively.

Figure 14:
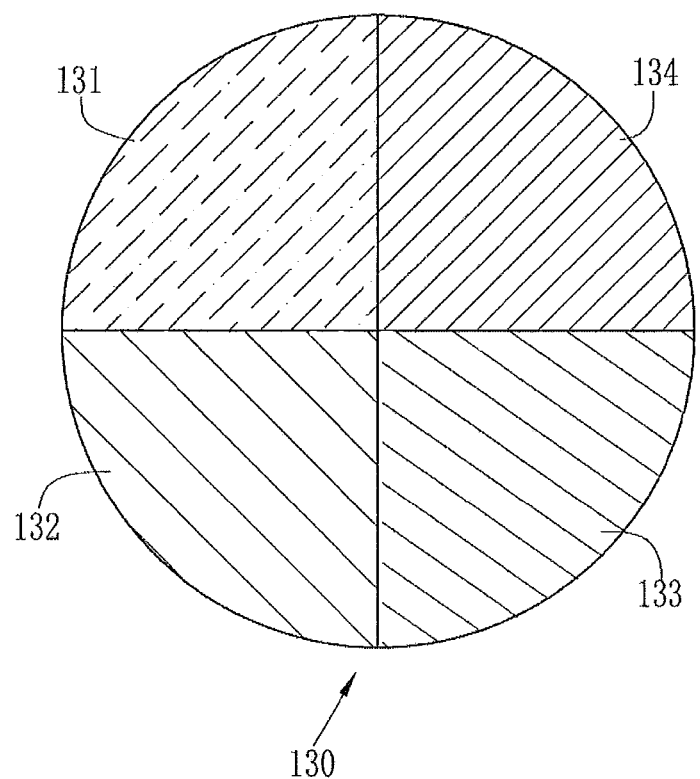
FIG. 14 is a schematic view of a rotary filter.

The optical filter may for example be a rotary filter 130 as illustrated in FIG. 14. The rotary filter 130 comprises a broadband light transmission region 131 for passing the broadband light 133 from the broadband light source 30 as it is, a first narrowband light transmission region 132 for passing the first narrowband light N1 out of the broadband light BB, a second narrowband light transmission region 133 for passing the second narrowband light N2 out of the broadband light BB, and a third narrowband light transmission region 134 for passing the third narrowband light N3 out of the broadband light BB. The rotary filter 130 is capable of rotation and turned so as to place the broadband light transmission region 131 on the optical path of the broadband light source 30 to produce the broadband light BB and place one of the first to the third narrowband light transmission regions 132 to 134 on the optical path of the broadband light source 30 to produce the corresponding one of the first narrowband light N1 to N3.

The electronic endoscope system 110 according to the third embodiment operates basically similarly to the electronic endoscope system according to the second embodiment. Thus, redundant descriptions will not be made, focusing instead on unshared features, which are the steps S26 onward in the flowchart illustrated in FIGS. 11 and 12.

According to the third embodiment of the invention, the luminance ratio calculator 60 calculates a third luminance ratio S3*/S1* in lieu of the step S26.

The third luminance ratio S3*/S1* is an image signal ratio at a given pixel between two images acquired by illumination of light having wavelengths of 500 nm and 540, respectively. The pixel value ratio S(500)/S(540) tends to be particularly small in the case of a thick blood vessel located in an intermediate or deeper layer. The thick blood vessel here denotes a blood vessel having a diameter of 100 µm or more located in an intermediate or deeper layer (in a depth of 100 µm or more) of a digestive tract mucosa of interest.

The reference value region setter 210 performs threshold processing of all the pixels in the blood vessel region in respect of the third luminance ratio to identify a region whose third luminance ratio is small. That is, the processing determines whether a pixel of interest belongs to a thick blood vessel (deep-layer blood vessel) region. Next, out of the blood vessel region, said thick blood vessel region is automatically designated as a reference value region. The reference value region may be the whole thick blood vessel region or a given position in the thick blood vessel region or a region therein having a given size.

Next, the luminance ratio calculator 60 calculates a fourth luminance ratio S1*/S2* for the thick blood vessel region set as the reference value region. The fourth luminance ratio S1*/S2* is an image signal ratio at a given pixel between two images acquired by illumination of light having wavelengths of 540 nm and 560 nm, respectively. The pixel value ratio S(540)/S(560) tends to increase with the oxygen saturation level.

The thick blood vessel region is either an artery or a vein and when in normal state typically has an oxygen saturation level of about 100% and 70%, respectively. Therefore, the distribution of the fourth luminance ratio in the reference value region is obtained, and a mean value of the upper 20% is assigned to an oxygen saturation level of 100% while the lower 20% is assigned to an oxygen saturation level of 70%, which are used respectively as first reference value oxygen saturation level information and second reference value oxygen saturation level information. Thus, an artery is expressed in a relative value with respect to the first reference value oxygen saturation level information as a reference; a vein is expressed in a relative value with respect to the second reference value oxygen saturation level information as a reference. The other part than the artery and the vein are for example assigned relative values obtained by dividing the difference between the values of the first and the second reference value oxygen saturation level information at equal intervals to produce the relative value oxygen saturation level image for the while blood vessel region.

Figure 15:
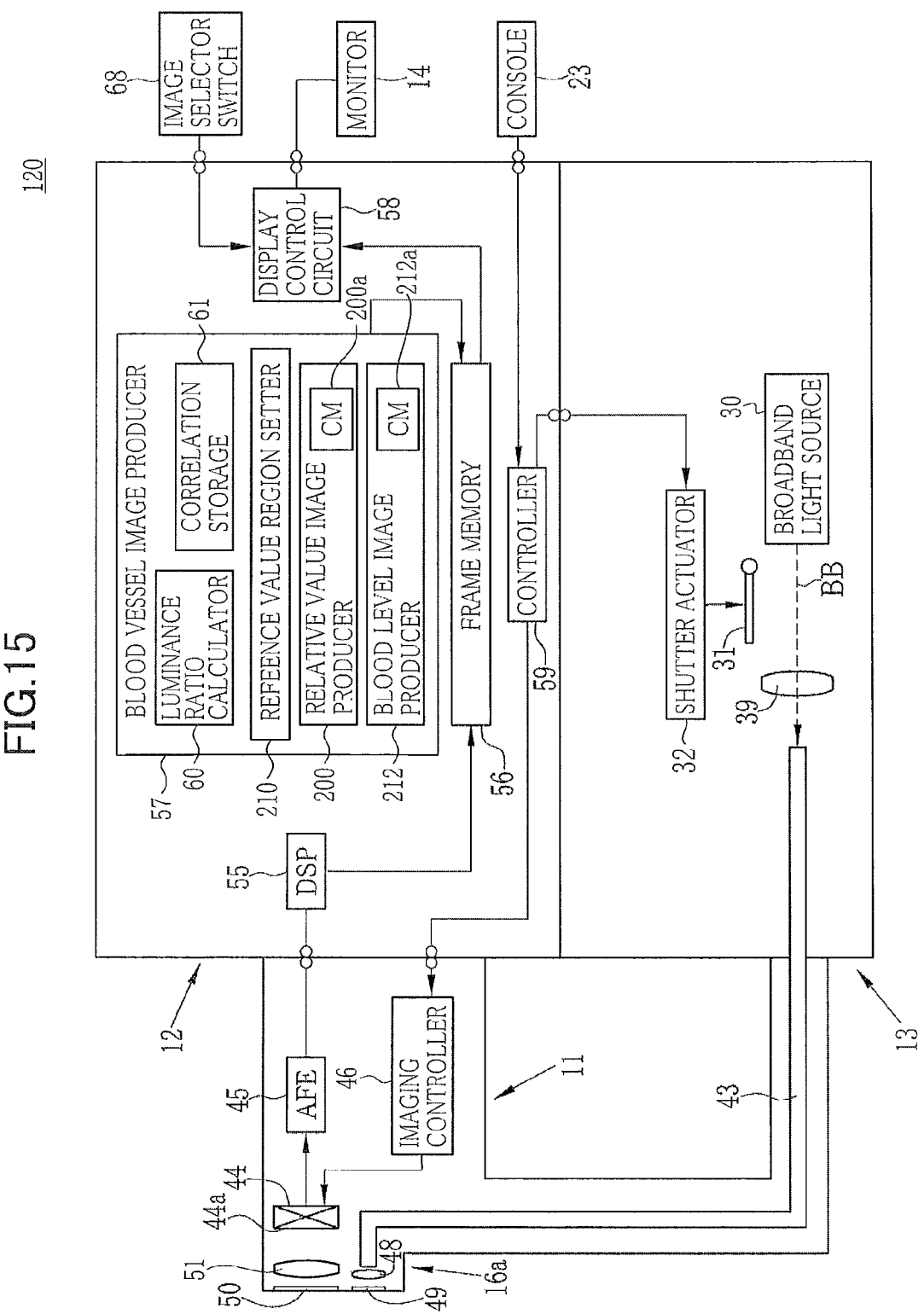
FIG. 15 is a block diagram illustrating an electric configuration of the electronic endoscope system according to a fourth embodiment of the invention.

FIG. 15 is a block diagram illustrating a configuration of an electronic endoscope system 120, a fourth embodiment of the invention different from the first to the third embodiments described above.

As compared with the electronic endoscope system according to the first embodiment illustrated in FIG. 2, the electronic endoscope system 120 basically has the same configuration except that the broadband light directly illuminates the inside of a body cavity and that images of the R-channel and the G-channel of the CCD are used in lieu of those acquired using the narrowband light. Thus, like components are given like reference characters, and detailed descriptions thereof will be omitted below.

Similar to the oxygen saturation level image producer 64 in the first embodiment, a blood level image producer 212 has a color map 212a (CM) where color information is assigned according to the blood level. The blood level image producer 212 determines color information corresponding to a signal ratio G/R (absolute value blood level information) calculated by the luminance ratio calculator 60 using the color map 212a.

When all the pixels in the blood vessel region have been assigned color information, the blood level image producer 212 reads out broadband image data from the frame memory 56 and incorporates the color information in the read-out broadband image data. Thus, the absolute value blood level image data incorporating absolute value blood level information is produced.

As described above, the electronic endoscope system 120 according to the fourth embodiment operates basically similarly to the electronic endoscope system according to the first embodiment except that the broadband light directly illuminates the inside of the body cavity and that images of the R-channel and the G-channel of the CCD are used in lieu of those acquired using the narrowband light. Thus, descriptions will be made below omitting redundancies.

According to the fourth embodiment of the invention, the broadband light emitted from the broadband light source 30 illuminates the inside of the body cavity, whereupon the operator operates the console 23 to perform freeze operation for acquiring a still image and obtain a broadband imaging signal as in the normal light image mode according to the first embodiment.

The luminance ratio calculator 60 calculates the signal ratio G/R, a pixel value ratio between an imaging signal G and an imaging signal R of the acquired broadband imaging signal. The signal ratio G/R is the absolute value blood level information and corresponds to the absolute value oxygen saturation level information in the first embodiment. The image data composed of imaging signal G and the imaging signal R correspond to the first and the second narrowband image data in the first embodiment, respectively.

The signal ratio G/R is an image signal ratio between two images of the R channel and the G channel of the CCD 44 and tends to decrease as the blood level increases, that is, as the hemoglobin concentration in blood increases. The absolute value blood level information may be the logarithm of the signal ratio G/R as well as the signal ratio G/R.

Thereafter, as in the first embodiment, the blood level image producer 212 produces the absolute value blood level image data. Then, the operator operates the console 23 to cause the reference value region setter 210 to set the reference value region, thus producing the reference value blood level information from a mean value of the absolute value blood level information in the reference value region. Further, the difference between the absolute value blood level information and the reference value blood level information in the whole blood vessel region is calculated to produce the relative value blood level information and, hence, the relative value blood level image, a simulated color image, may be produced.

As described above, the first embodiment of the invention allows the simulated color display of the oxygen saturation level to be switched as desired between the absolute value display mode and the relative value display mode according to the input made by the operator. The second embodiment of the invention automatically identifies the non-superficial-layer blood vessel region and designates it as the reference value region and permits simulated color display of the relative value oxygen saturation level. Further, the third embodiment of the invention identifies the thick blood vessel region and permits simulated color display of the relative value oxygen saturation level of the thick blood vessel region to allow easy distinction between an artery and a vein. Further, the fourth embodiment of the invention allows the simulated color display of the blood level to be switched as desired between the absolute value display mode and the relative value display mode according to the input made by the operator. Such relative value display permits improvement of the robustness of the oxygen saturation level and the blood level.

Although the first to the third narrowband light sources are used to obtain the blood vessel depth and the oxygen saturation level according to the first and the second embodiments, a fourth narrowband light source for producing a fourth narrowband light N4 having a wavelength limited to a proximity of 532 nm may be added in order to produce the first to the fourth narrowband image data by illumination with the first to the fourth narrowband light N1 to N4, so that the blood vessel depth and the oxygen saturation level may be obtained based on these image data. Because light reaches an increasingly deeper layer as its wavelength grows longer, information on a blood vessel located at a still deeper position may be obtained using the fourth narrowband light N4 having a wavelength longer than that of the second narrowband light N2.

In this case, the luminance ratio calculator 60 determines the blood vessel region from the first to the fourth narrowband image data. Further, as in the first embodiment, the first and the second luminance ratios S1/S3 and S2/S3 are obtained as well as the third luminance ratio S4/S3, which is a luminance ratio between the first and the fourth narrowband image data. S4 is the luminance value of a pixel in the fourth narrowband image data. The blood vessel depth-oxygen saturation level calculator 62 calculates the blood vessel depth information and the oxygen saturation level information corresponding to the first to the third luminance ratios calculated by the luminance ratio calculator 60 through the same procedure as in the first embodiment based on the correlation, previously obtained by conducting experiment and the like, between the first to the third luminance ratios S1/S3, S2/S3, and S4/S3 and the blood vessel depth and oxygen saturation level.

The number of frames of the imaging signal may be reduced by achieving imaging with illumination using synthesized light obtained by combining two or more of the first to the fourth narrowband light N1 to N4 in lieu of executing imaging each time illumination is effected by the first to the fourth narrowband light N1 to N4. For example, the inside of the body cavity may first be imaged by simultaneous illumination with the first narrowband light N1 and the fourth narrowband N4. The inside of the body cavity may then be imaged by simultaneous illumination with the second narrowband light N2 and the third narrowband N3. Thus, a total of two frames of imaging signals are obtained.

The imaging signal obtained by the first imaging comprises an imaging signal B1 and an imaging signal G1 having the following luminance values, respectively. The imaging signal obtained by the next imaging comprises an imaging signal B2 and an imaging signal G2 having the following luminance values, respectively.

The imaging signal B1 has a luminance value L1+L4, where L1 is the luminance value resulting from the first narrowband light N1, and L4 is the luminance value resulting from the fourth narrowband light N4.

The imaging signal G1 has a luminance value L4, which is the luminance value resulting from the fourth narrowband light N4.

The imaging signal B2 has a luminance value L2+L3, where L2 is the luminance value resulting from the second narrowband light N2, and L3 is the luminance value resulting from the third narrowband light N3.

The imaging signal G2 has a luminance value L2, which is the luminance value resulting from the second narrowband light N2.

The imaging signal G2 having only the luminance value L2 yields the second narrowband image data; the imaging signal G1 having only the luminance value L4 yields the fourth narrowband image data. Computation of B1−(constant)×G1 separates the luminance value L4 from the imaging signal B1, producing the first narrowband image data. The constant is determined from the intensity ratio between the first narrowband light N1 and the fourth narrowband light N4. Further, computation of B2−(constant)×G2 separates the luminance value L3 from the imaging signal B2, producing the second narrowband image data. The constant is determined from the intensity ratio between the second narrowband light N2 and the third narrowband light N3.

Although, according to the first and the fourth embodiments, the operator sets the reference value region after the absolute value oxygen saturation level image or the absolute value blood level image is once displayed, the procedure may be such that the operator sets the reference value region on the broadband image before the absolute value oxygen saturation level image or the absolute value blood level image is displayed. According to the second embodiment, in lieu of the display order in which the broadband image is first displayed, and then the absolute value oxygen saturation level image, followed by the relative value oxygen saturation level image, the broadband image may be followed by the relative value oxygen saturation level image in the order of display.

Although the first and the second embodiments use the first to the third narrowband light sources to produce the first to the third narrowband light N1 to N3, the first to the third narrowband light N1 to N3 may be produced using the rotary filter 130 illustrated in FIG. 14 as in The third embodiment without providing the first to the third narrowband light sources.

The present invention may be applied not only to an insertion type electronic endoscope comprising an insertion section as described above but also to a capsule type electronic endoscope comprising an image sensor and the like such as a CCD incorporated in a capsule.

While the electronic endoscope system, the electronic endoscope processor, and the method of acquiring blood vessel information according to the present invention have been described above in detail, the present invention is by no means limited to the above embodiments and various improvements and modifications may of course be made without departing from the spirit of the present invention.

I claim:

1. An electronic endoscope system comprising:
    an illuminating means for illuminating a subject tissue located in a body cavity and containing a blood vessel with illumination light,
    an electronic endoscope including an image sensor for receiving reflected light of the illumination light emitted from the illuminating means to the subject tissue to acquire an image of the subject tissue and outputting an imaging signal representing a luminance of the reflected light,
    a first image data producing means for outputting a plurality of first image data having different wavelength bands from the imaging signal,
    a blood vessel information producing means for producing blood vessel information on the blood vessel from the first image data,
    a reference value region setting means for setting a given region in an image acquired by the electronic endoscope as reference value region,
    a reference value blood vessel information calculating means for calculating a reference value for the blood vessel information based on second image data for a region within a reference value region set by the reference value region setting means to acquire a reference value blood vessel information,
    a relative value blood vessel information calculating means for calculating relative value blood vessel information from a difference between the blood vessel information and the reference value blood vessel information,
    an image producing means for producing a relative value blood vessel information image representing a relative value of the blood vessel information in simulated color from the relative value blood vessel information, and
    an image displaying means for displaying a relative value blood vessel information image produced by the image producing means;
    wherein the imaging signal is a first narrowband signal, a second narrowband signal, and a third narrowband signal respectively corresponding to a first narrowband light, a second narrowband light, and a third narrowband light having different wavelength bands,
    wherein the blood vessel information is an oxygen saturation level of blood hemoglobin in the blood vessel, and
    wherein the reference value region setting means calculates a first luminance ratio between the first image data respectively corresponding to the first narrowband signal and the third narrowband signal and a second luminance ratio between the first image data respectively corresponding to the second narrowband signal and the third narrowband signal, further calculates blood vessel depth information from the first luminance ratio and the second luminance ratio, distinguishes between superficial-layer blood vessel region and a non-superficial-layer blood vessel region from the blood vessel depth information, and thereby sets the non-superficial-layer blood vessel region as the reference value region.

2. The electronic endoscope system according to claim 1, wherein the image producing means further produces an absolute value blood vessel information image representing an absolute value of the blood vessel information in simulated color from the blood vessel information produced by the blood vessel information producing means,
    wherein the electronic endoscope system further comprises an image switching means for switching between the absolute value blood vessel information image and the relative value blood vessel information image, and
    wherein the image displaying means displays one of the absolute value blood vessel information image and the relative value blood vessel information image selected by the image switching means.

3. The electronic endoscope system according to claim 1, wherein the first and the second narrowband light exhibit different absorbances for oxygenated hemoglobin, which is combined with oxygen, and reduced hemoglobin, which is not combined with oxygen, and include wavelengths producing a difference in absorbance by each hemoglobin according to oxygen saturation level.

4. The electronic endoscope system according to claim 1, wherein the first narrowband light has a wavelength range of 440 nm plus or minus 10 nm, the second narrowband light has a wavelength range of 470 nm plus or minus 10 nm, and the third narrowband light has a wavelength range of 400 nm plus or minus 10 nm.

5. The electronic endoscope system according to claim 1,
wherein the image sensor comprises pixels having three colors, red pixels, green pixels, and blue pixels, each provided with color filters having three colors, red, green, and blue,
wherein the imaging signal contains an imaging signal of a green pixel and an imaging signal of a red pixel, and
wherein the blood vessel information is a blood level.

6. The electronic endoscope system according to claim 1, wherein the reference value region setting means sets as the reference value region a given region entered by an operator of the electronic endoscope system in an image acquired by the electronic endoscope.

7. A processor for an electronic endoscope comprising:
a signal receiving means for receiving from the electronic endoscope an imaging signal obtained by imaging reflected light of illumination light illuminating a subject tissue located in a body cavity and containing a blood vessel with an image sensor of the electronic endoscope, the imaging signal representing a luminance of the reflected light,
a first image data producing means for outputting a plurality of first image data having different wavelength bands from the imaging signal,
a blood vessel information producing means for producing blood vessel information on the blood vessel from the first image data,
a reference value region setting means for setting a given region in an image acquired by the electronic endoscope as reference value region,
a reference value blood vessel information calculating means for calculating a reference value for the blood vessel information based on second image data for a region within a reference value region set by the reference value region setting means to acquire reference value blood vessel information,
a relative value blood vessel information calculating means for calculating relative value blood vessel information from a difference between the blood vessel information and the reference value blood vessel information,
an image producing means for producing a relative value blood vessel information image representing a relative value of the blood vessel information in simulated color from the relative value blood vessel information, and
an image displaying means for displaying a relative value blood vessel information image produced by the image producing means;
wherein the imaging signal is a first narrowband signal, a second narrowband signal, and a third narrowband signal respectively corresponding to a first narrowband light, a second narrowband light, and a third narrowband light having different wavelength bands,
wherein the blood vessel information is an oxygen saturation level of blood hemoglobin in the blood vessel, and
wherein the reference value region setting means calculates a first luminance ratio between the first image data respectively corresponding to the first narrowband signal and the third narrowband signal and a second luminance ratio between the first image data respectively corresponding to the second narrowband signal and the third narrowband signal, further calculates blood vessel depth information from the first luminance ratio and the second luminance ratio, distinguishes between superficial-layer blood vessel region and a non-superficial-layer blood vessel region from the blood vessel depth information, and thereby sets the non-superficial-layer blood vessel region as the reference value region.

8. A pathological observation device comprising:
an illuminating means for illuminating a subject tissue located in a body cavity and containing a blood vessel with illumination light,
an observing means including an image sensor for receiving reflected light of the illumination light emitted from the illuminating means to the subject tissue, acquiring an image of the subject tissue, and outputting an imaging signal representing a luminance of the reflected light,
a first image data producing means for outputting a plurality of first image data having different wavelength bands from the imaging signal,
a blood vessel information producing means for producing blood vessel information on the blood vessel from the first image data,
a reference value region setting means for setting a given region in an image acquired by the electronic endoscope as reference value region,
a reference value blood vessel information calculating means for calculating a reference value for the blood vessel information based on second image data for a region within a reference value region set by the reference value region setting means to acquire a reference value blood vessel information,
a relative value blood vessel information calculating means for calculating relative value blood vessel information from a difference between the blood vessel information and the reference value blood vessel information,
an image producing means for producing a relative value blood vessel information image representing a relative value of the blood vessel information in simulated color from the relative value of blood vessel information, and
an image displaying means for displaying a relative value blood vessel information image produced by the image producing means;
wherein the imaging signal is a first narrowband signal, a second narrowband signal, and a third narrowband signal respectively corresponding to a first narrowband light, a second narrowband light, and a third narrowband light having different wavelength bands,
wherein the blood vessel information is an oxygen saturation level of blood hemoglobin in the blood vessel, and
wherein the reference value region setting means calculates a first luminance ratio between the first image data respectively corresponding to the first narrowband signal and the third narrowband signal and a second luminance ratio between the first image data respectively corresponding to the second narrowband signal and the third narrowband signal, further calculates blood vessel depth information from the first luminance ratio and the second luminance ratio, distinguishes between superficial-layer blood vessel region and a non-superficial-layer blood vessel region from the blood vessel depth information, and thereby sets the non-superficial-layer blood vessel region as the reference value region.

9. A pathological microscope device comprising:
an illuminating means for illuminating a subject tissue located in a body cavity and containing a blood vessel with illumination light,
an observing means including an image sensor for receiving reflected light of the illumination light emitted from the illuminating means to the subject tissue, acquiring an image of the subject tissue, and outputting an imaging signal representing a luminance of the reflected light,
a first image data producing means for outputting a plurality of first image data having different wavelength bands from the imaging signal, a blood vessel information producing means for producing blood vessel information on the blood vessel from the first image data, a reference value region setting means for setting a given region in an image acquired by the electronic endoscope as reference value region, a reference value blood vessel information calculating means for calculating a reference value for the blood vessel information based on second image data for a region within a reference value region set by the reference value region setting means to acquire a reference value blood vessel information, a relative value blood vessel information calculating means for calculating relative value blood vessel information from a difference between the blood vessel information and the reference value blood vessel information, an image producing means for producing a relative value blood vessel information image representing a relative value of the blood vessel information in simulated color from the relative value blood vessel information, and an image displaying means for displaying a relative value blood vessel information image produced by the image producing means;

wherein the imaging signal is a first narrowband signal, a second narrowband signal, and a third narrowband signal respectively corresponding to a first narrowband light, a second narrowband light, and a third narrowband light having different wavelength bands, wherein the blood vessel information is an oxygen saturation level of blood hemoglobin in the blood vessel, and wherein the reference value region setting means calculates a first luminance ratio between the first image data respectively corresponding to the first narrowband signal and the third narrowband signal and a second luminance ratio between the first image data respectively corresponding to the second narrowband signal and the third narrowband signal, further calculates blood vessel depth information from the first luminance ratio and the second luminance ratio, distinguishes between superficial-layer blood vessel region and a non-superficial-layer blood vessel region from the blood vessel depth information, and thereby sets the non-superficial-layer blood vessel region as the reference value region.

10. An electronic endoscope system comprising:

an illuminating means for illuminating a subject tissue located in a body cavity and containing a blood vessel with illumination light, an electronic endoscope including an image sensor for receiving reflected light of the illumination light emitted from the illuminating means to the subject tissue to acquire an image of the subject tissue and outputting an imaging signal representing a luminance of the reflected light, a first image data producing means for outputting a plurality of first image data having different wavelength bands from the imaging signal, a blood vessel information producing means for producing blood vessel information on the blood vessel from the first image data, a reference value region setting means for setting a given region in an image acquired by the electronic endoscope as reference value region, a reference value blood vessel information calculating means for calculating a reference value for the blood vessel information based on second image data for a region within a reference value region set by the reference value region setting means to acquire a reference value blood vessel information, a relative value blood vessel information calculating means for calculating relative value blood vessel information from a difference between the blood vessel information and the reference value blood vessel information, an image producing means for producing a relative value blood vessel information image representing a relative value of the blood vessel information in simulated color from the relative value blood vessel information, and an image displaying means for displaying a relative value blood vessel information image produced by the image producing means;

wherein the imaging signal is a first narrowband signal, a second narrowband signal, and a third narrowband signal respectively corresponding to a first narrowband light, a second narrowband light, and a third narrowband light, the first narrowband light having a wavelength range of 540 nm plus or minus 10 nm, the second narrowband light having a wavelength range of 560 nm plus or minus 10 nm, and the third narrowband light having a wavelength range of 500 nm plus or minus 10 nm, wherein the blood vessel information is an oxygen saturation level of blood hemoglobin in the blood vessel, wherein the reference value region setting means further calculates a third luminance ratio between the first image data respectively corresponding to the third narrowband signal and the first narrowband signal, identifies a thick blood vessel region based on the third luminance ratio, sets the thick blood vessel region as the reference value region, and calculates a fourth luminance ratio between the first image data respectively corresponding to the first narrowband signal and the second narrowband signal, and wherein the image producing means produce a relative value oxygen saturation level image based on a distribution of the fourth luminance ratio.

11. A processor for an electronic endoscope comprising:

a signal receiving means for receiving from the electronic endoscope an imaging signal obtained by imaging reflected light of illumination light illuminating a subject tissue located in a body cavity and containing a blood vessel with an image sensor of the electronic endoscope, the imaging signal representing a luminance of the reflected light, a first image data producing means for outputting a plurality of first image data having different wavelength bands from the imaging signal, a blood vessel information producing means for producing blood vessel information on the blood vessel from the first image data, a reference value region setting means for setting a given region in an image acquired by the electronic endoscope as reference value region, a reference value blood vessel information calculating means for calculating a reference value for the blood vessel information based on second image data for a region within a reference value region set by the reference value region setting means to acquire reference value blood vessel information, a relative value blood vessel information calculating means for calculating relative value blood vessel information from a difference between the blood vessel information and the reference value blood vessel information, an image producing means for producing a relative value blood vessel information image representing a relative value of the blood vessel information in simulated color from the relative value blood vessel information, and an image displaying means for displaying a relative value blood vessel information image produced by the image producing means;

wherein the imaging signal is a first narrowband signal, a second narrowband signal, and a third narrowband signal respectively corresponding to a first narrowband light, a second narrowband light, and a third narrowband light, the first narrowband light having a wavelength range of 540 nm plus or minus 10 nm, the second narrowband light having a wavelength range of 560 nm plus or minus 10 nm, and the third narrowband light having a wavelength range of 500 nm plus or minus 10 nm, wherein the blood vessel information is an oxygen saturation level of blood hemoglobin in the blood vessel, wherein the reference value region setting means further calculates a third luminance ratio between the first image data respectively corresponding to the third narrowband signal and the first narrowband signal, identifies a thick blood vessel region based on the third luminance ratio, sets the thick blood vessel region as the reference value region, and calculates a fourth luminance ratio between the first image data respectively corresponding to the first narrowband signal and the second narrowband signal, and wherein the image producing means produce a relative value oxygen saturation level image based on a distribution of the fourth luminance ratio.

12. A pathological observation device comprising:

an illuminating means for illuminating a subject tissue located in a body cavity and containing a blood vessel with illumination light, an observing means including an image sensor for receiving reflected light of the illumination light emitted from the illuminating means to the subject tissue, acquiring an image of the subject tissue, and outputting an imaging signal representing a luminance of the reflected light, a first image data producing means for outputting a plurality of first image data having different wavelength bands from the imaging signal, a blood vessel information producing means for producing blood vessel information on the blood vessel from the first image data, a reference value region setting means for setting a given region in an image acquired by the electronic endoscope as reference value region, a reference value blood vessel information calculating means for calculating a reference value for the blood vessel information based on second image data for a region within a reference value region set by the reference value region setting means to acquire a reference value blood vessel information, a relative value blood vessel information calculating means for calculating relative value blood vessel information from a difference between the blood vessel information and the reference value blood vessel information, an image producing means for producing a relative value blood vessel information image representing a relative value of the blood vessel information in simulated color from the relative value of blood vessel information, and an image displaying means for displaying a relative value blood vessel information image produced by the image producing means;

wherein the imaging signal is a first narrowband signal, a second narrowband signal, and a third narrowband signal respectively corresponding to a first narrowband light, a second narrowband light, and a third narrowband light, the first narrowband light having a wavelength range of 540 nm plus or minus 10 nm, the second narrowband light having a wavelength range of 560 nm plus or minus 10 nm, and the third narrowband light having a wavelength range of 500 nm plus or minus 10 nm, wherein the blood vessel information is an oxygen saturation level of blood hemoglobin in the blood vessel, wherein the reference value region setting means further calculates a third luminance ratio between the first image data respectively corresponding to the third narrowband signal and the first narrowband signal, identifies a thick blood vessel region based on the third luminance ratio, sets the thick blood vessel region as the reference value region, and calculates a fourth luminance ratio between the first image data respectively corresponding to the first narrowband signal and the second narrowband signal, and wherein the image producing means produce a relative value oxygen saturation level image based on a distribution of the fourth luminance ratio.

13. A pathological microscope device comprising:

an illuminating means for illuminating a subject tissue located in a body cavity and containing a blood vessel with illumination light, an observing means including an image sensor for receiving reflected light of the illumination light emitted from the illuminating means to the subject tissue, acquiring an image of the subject tissue, and outputting an imaging signal representing a luminance of the reflected light, a first image data producing means for outputting a plurality of first image data having different wavelength bands from the imaging signal, a blood vessel information producing means for producing blood vessel information on the blood vessel from the first image data, a reference value region setting means for setting a given region in an image acquired by the electronic endoscope as reference value region, a reference value blood vessel information calculating means for calculating a reference value for the blood vessel information based on second image data for a region within a reference value region set by the reference value region setting means to acquire a reference value blood vessel information, a relative value blood vessel information calculating means for calculating relative value blood vessel information from a difference between the blood vessel information and the reference value blood vessel information, an image producing means for producing a relative value blood vessel information image representing a relative value of the blood vessel information in simulated color from the relative value blood vessel information, and an image displaying means for displaying a relative value blood vessel information image produced by the image producing means;

wherein the imaging signal is a first narrowband signal, a second narrowband signal, and a third narrowband signal respectively corresponding to a first narrowband light, a second narrowband light, and a third narrowband light, the first narrowband light having a wavelength range of 540 nm plus or minus 10 nm, the second narrowband light having a wavelength range of 560 nm plus or minus 10 nm, and the third narrowband light having a wavelength range of 500 nm plus or minus 10 nm, wherein the blood vessel information is an oxygen saturation level of blood hemoglobin in the blood vessel, wherein the reference value region setting means further calculates a third luminance ratio between the first image data respectively corresponding to the third narrowband signal and the first narrowband signal, identifies a thick blood vessel region based on the third luminance ratio, sets the thick blood vessel region as the reference value region, and calculates a fourth luminance ratio between the first image data respectively corresponding to the first narrowband signal and the second narrowband signal, and wherein the image producing means produce a relative value oxygen saturation level image based on a distribution of the fourth luminance ratio.

* * * * *